(12) United States Patent
Sarkar et al.

(10) Patent No.: US 9,283,244 B2
(45) Date of Patent: Mar. 15, 2016

(54) TREATMENT OF CANCER BY INHIBITING ACTIVITY OR EXPRESSION OF LATE SV-40 FACTOR

(75) Inventors: Devanand Sarkar, Richmond, VA (US); Paul B. Fisher, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 268 days.

(21) Appl. No.: 13/636,815

(22) PCT Filed: Mar. 29, 2011

(86) PCT No.: PCT/US2011/030293
§ 371 (c)(1),
(2), (4) Date: Sep. 24, 2012

(87) PCT Pub. No.: WO2011/123427
PCT Pub. Date: Oct. 6, 2011

(65) Prior Publication Data
US 2013/0028899 A1    Jan. 31, 2013

Related U.S. Application Data

(60) Provisional application No. 61/319,991, filed on Apr. 1, 2010, provisional application No. 61/467,430, filed on Mar. 25, 2011.

(51) Int. Cl.
*A61K 31/70* (2006.01)
*C07H 21/02* (2006.01)
*C07H 21/04* (2006.01)
*A61K 31/7105* (2006.01)
*C07K 16/18* (2006.01)
*C07K 16/30* (2006.01)
*C12Q 1/68* (2006.01)
*G01N 33/574* (2006.01)
*C12N 5/00* (2006.01)
*A61K 39/00* (2006.01)

(52) U.S. Cl.
CPC ............ *A61K 31/7105* (2013.01); *C07K 16/18* (2013.01); *C07K 16/303* (2013.01); *C12Q 1/6886* (2013.01); *G01N 33/57438* (2013.01); *A61K 2039/505* (2013.01); *C12Q 2600/112* (2013.01); *C12Q 2600/118* (2013.01); *C12Q 2600/136* (2013.01); *C12Q 2600/158* (2013.01)

(58) Field of Classification Search
None
See application file for complete search history.

(56) References Cited

U.S. PATENT DOCUMENTS

2009/0131423 A1* 5/2009 Dinsmore et al. ......... 514/232.8
2009/0175860 A1* 7/2009 Stover et al. ............... 424/133.1

OTHER PUBLICATIONS

Sarkar et al., Molecular Therapy vol. 17, Supplement 1:S382, May 2009.*

* cited by examiner

*Primary Examiner* — Sean McGarry
(74) *Attorney, Agent, or Firm* — Whitham, Curtis, Christofferson & Cook, P.C.

(57) ABSTRACT

Inhibitors of Late SV-40 Factor (LSF) are used to treat cancers such as hepatocellular carcinoma (HCC). In particular, small molecule chemical LSF inhibitors are employed. In addition, the activity and/or pattern of expression of LSF may is used to diagnose cancer, to characterize the cancer (e.g. stage, grade, prognosis, etc.) and also to develop suitable protocols for cancer treatment.

6 Claims, 29 Drawing Sheets

M: Molecular Wt Marker
1: No template
2: Input DNA
3: No Ab
4: Normal IgG
5: Anti-LSF Ab

TREATMENT OF CANCER BY INHIBITING ACTIVITY OR EXPRESSION OF LATE SV-40 FACTOR

CROSS-REFERENCE TO RELATED APPLICATIONS

This application is a 371 of International Application Number PCT/US2011/030293 filed Mar. 29, 2011, which claims benefit of U.S. provisional applications 61/319,991 filed Apr. 1, 2010 and 61/467,430 filed Mar. 25, 2011, all of which are incorporated herein by reference.

SEQUENCE LISTING

This application includes as the Sequence Listing the complete contents of the accompanying text file "Sequence.txt", created Mar. 24, 2011 containing 4,096 bytes, hereby incorporated by reference.

BACKGROUND OF THE INVENTION

1. Field of the Invention

The invention generally relates to cancer treatment, and particularly to the treatment of Hepatocellular carcinoma (HCC) and similar cancers. In particular, the invention provides methods for treating cancers by the inhibition of Late SV-40 Factor (LSF). Inhibition of LSF may be achieved by physical or chemical treatment (e.g., in vivo administration of inhibitors). Experimentation presented herein has shown that LSF is an effective target for cancer therapy.

2. Background of the Invention

Hepatocellular carcinoma (HCC) is one of the five most common cancers worldwide (1). The incidence of HCC is increasing despite a decrease in overall incidence of all cancers (2, 3). In the US, the estimated new cases of HCC for 2008 was 21,370 out of which 18,410 were expected to die (2). The mortality rate of HCC parallels that of incidence since HCC is a tumor with rapid growth and early vascular invasion that is resistant to conventional chemotherapy and no systemic therapy is available for the advanced disease (4). As such, understanding the molecular mechanism of HCC development and progression is imperative to establish novel, effective and targeted therapies for this highly aggressive cancer.

Recent studies have revealed that Astrocyte Elevated Gene-1 (AEG-1) is overexpressed in >90% of human HCC patients, compared to normal liver, and AEG-1 plays a key role in regulating development and progression of HCC (5). The transcription factor Late SV40 Factor (LSF) has been identified as a downstream gene of AEG-1 and it has been demonstrated that LSF mediates, in part, AEG-1-induced resistance to 5-fluorouracil (5-FU) in HCC cells (5, 6). LSF, also known as LBP-1c and TFCP2, regulates diverse cellular and viral promoters (7, 8). A major cellular target of LSF is the thymidylate synthase (TS) gene which encodes the rate limiting enzyme in the production of dTTP, required for DNA synthesis (9). Inhibition of LSF abrogates TS induction and induces apoptosis. Thus LSF plays an important role in DNA synthesis and cell survival. In the liver, LSF is activated by inflammatory cytokines and regulates the expression of acute phase proteins (10, 11). In addition, Inhibition of LSF is known to induce S-phase-dependent apoptosis by down-regulating thymidylate synthase expression (15). However, prior to the present disclosure, no studies have linked LSF to cancer or to the process of tumorigenesis. Further, no regulatory elements have previously been described for HCC.

SUMMARY OF THE INVENTION

Data described herein demonstrates the surprising finding that LSF is overexpressed in cancer cells, including HCC cells, and that inhibition of LSF causes a marked inhibition of solid tumor growth in vivo. Thus, the present invention provides methods of treating cancers such as hepatocellular carcinoma (HCC) by the inhibition of LSF. In addition, the invention provides methods of using LSF as a marker or indicator with respect to cancer, e.g. as a diagnostic tool, and/or as an indicator of the stage and aggressiveness of the cancer, and hence of the prognosis of the disease. A skilled practitioner can use this information to develop suitable cancer therapy protocols.

It is an object of the invention to provide methods of inhibiting or reducing tumor growth associated with cancer in vivo in a subject. The methods comprise the step of limiting expression or activity of Late SV40 Factor (LSF) activity in vivo in the subject. In some embodiments, the cancer is hepatocellular carcinoma (HCC). In other embodiments, the step of limiting includes a step of administering to the subject one or more of an LSF inhibitor compound, anti-LSF inhibitory RNA, and anti-LSF antibodies. In yet another embodiment, the LSF inhibitor compound targets at least one DNA binding domain of LSF, for example, an osteopontin (OPN) promoter binding domain.

The invention also provides methods of promoting damage or death of cancer cells in vivo in a subject. The methods comprise the step of limiting expression or activity of Late SV40 Factor (LSF) activity in vivo in the subject. In one embodiment, the cancer cells are from hepatocellular carcinoma (HCC). The step of limiting includes may include a step of administering to the subject one or more of an LSF inhibitor compound, anti-LSF inhibitory RNA, and anti-LSF antibodies. In some embodiments, the LSF inhibitor compound targets at least one DNA binding domain of LSF, for example, an osteopontin (OPN) promoter binding domain.

The invention also provides methods of determining a prognosis of a patient suffering from cancer. The methods comprise the steps of 1) obtaining, from the patient, a biological sample associated with the cancer; 2) measuring a level of expression or activity of Late SV40 Factor (LSF) in cells in the biological sample; 3) comparing the level of expression or activity of LSF in the cells in the biological sample to known reference levels of expression or activity of LSF; and, based on results obtained in the step of comparing, determining a prognosis of the patient with respect to the cancer. In some embodiments, the step of determining also includes a step of determining a grade or stage of the cancer. In other embodiments, the step of measuring also includes detecting the presence of absence of polysomy of an LSF gene in the cells from the biological sample. In further embodiments, the step of measuring also includes measuring a level of one or both of LSF mRNA and LSF protein, and in other embodiments, the method includes a step of measuring a level of expression or activity of a molecule from a pathway selected from the group consisting of MEK/ERK and NF-κB.

The invention also provides methods of diagnosing cancer in a patient in need thereof. The methods comprise the steps of 1) obtaining, from the patient, a biological sample which is suspected of being associated with cancer; 2) measuring a level of expression or activity of Late SV40 Factor (LSF) in cells in the biological sample; 3) comparing the level of expression or activity of LSF in the cells in the biological sample to known reference levels of expression or activity of LSF; and, if results obtained in the step of comparing show elevated levels of LSF activity or expression in the cells compared to the known reference levels, 4) concluding that the patient has cancer. In one embodiment, the cancer is hepatocellular carcinoma (HCC).

DETAILED DESCRIPTION

Figure 1B:
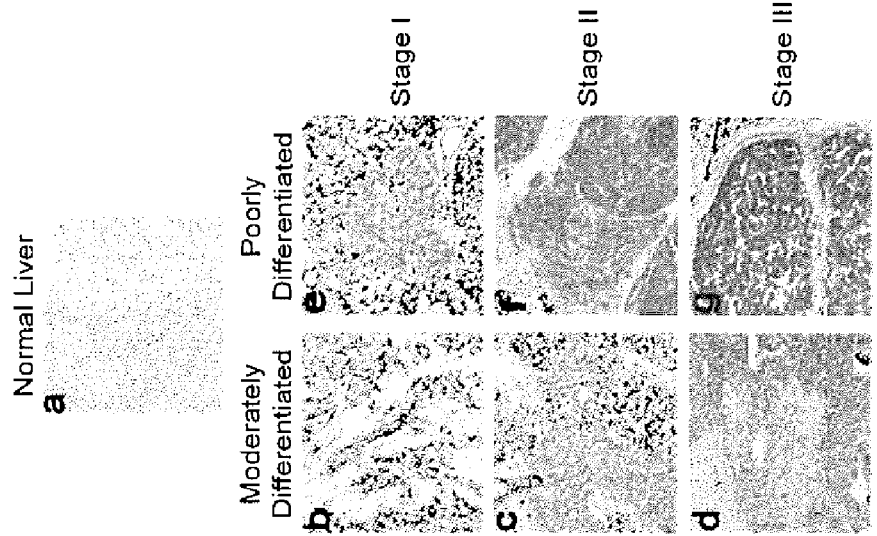
FIGS. 1A-C. LSF is overexpressed in HCC. A. LSF expression was detected by Western blot in the indicated cells. β-tubulin was used as loading control. B. Analysis of LSF expression in tissue microarray by immunohistochemistry. C. Fluorescence In Situ Hybridization (FISH) was performed on human HCC samples for LSF and D12Z3 (probe targeting pericentromeric region of chromosome 12). Red: LSF; green: D12Z3. Arrow indicates a cell displaying four signals for each of the probes, indicating 4 copies of these regions of chromosome 12.

The data presented herein demonstrates for the first time that LSF is a causative agent of cancers such as HCC.

This demonstration led to the discovery that inhibition of LSF can be used to successfully treat cancerous tumors (e.g. HCC tumors) in vivo.

Accordingly, methods of treating cancer by inhibition of LSF are described. Inhibition can be achieved by a number of modalities including by physical and chemical means (e.g., by providing a subject (human or animal) with an LSF inhibitor; by providing the subject with a physical treatment which inhibits LSF, etc.).

In addition, LSF expression and/or the genetic make-up of an individual with respect to LSF expression, can be determined and used as a marker or indicator with respect to cancer, e.g. as a diagnostic tool, and/or as an indicator of the stage and aggressiveness of the cancer, and hence of the prognosis of the disease. A skilled practitioner can use this information to develop suitable cancer therapy protocols.

In one embodiment, the invention provides methods of treating cancers using inhibitors of LSF. The inhibitors may be small or large molecules with the selection criteria being that they are safe for use in the subject and that they have the capability of inhibiting LSF upon administration to a subject.

In other embodiments, inhibition of the activity of LSF in a subject is carried out by affecting (e.g. down-regulating) the expression of LSF in a tumor cell. Exemplary strategies for inhibiting expression include but are not limited to, for example, the use of inhibitory RNA such as shRNA, antisense oligonucleotides, dominant negative constructs, etc.

In yet other embodiments, anti-LSF antibodies may be employed to inhibit LSF, and hence to treat or prevent cancers caused by LSF overactivity. Both polyclonal and monoclonal antibodies may be used, with monoclonal antibodies generally being preferred. In some embodiments, such antibodies are directed to (i.e. specific or selective for binding to) e.g. DNA binding sites or regions of LSF such as those which bind to the OPN promoter region.

In yet other embodiments, LSF is inhibited by binding to proteins, peptides or fragments thereof that are known to bind LSF, e.g. those described as "bait" and "prey" partners in US 2007/0225209 (which is herein incorporated by reference) such as preseniliin 1, amyloid A-beta protein precursor, the short isoform of 4F5 protein, etc.

In yet other embodiments, inhibition is not of LSF expression per se, but rather of another entity in a pathway that leads to LSF expression and/or activity is inhibited, i.e. LSF activity is inhibited indirectly. For example, osteopontin (OPN) and/or c-met expression or activity (or both) may be inhibited or attenuated, either separately, or in combination with LSF inhibition.

By "inhibiting" or "attenuating" (decreasing, lowering, etc.) the expression or activity of LSF, we mean that the level or LSF expression or activity that is detectable in a suitable sample (e.g. in a biological sample from a subject) is at least about 10, 20, 30, 40, 50, 60, 70, 80, 90 or even 100%, less than the level that is detected in a corresponding control sample. (100% less=no activity/expression detected). Typically, levels of expression/activity of control samples are determined and stored in a database, and the database is accessed using a computer in order to make the determination of activity/expression levels in an experimental sample from a subject. Various parameters may be detected, e.g. genetic makeup of cells in the sample (e.g. presence or absence of polysomy), levels of RNA (e.g. mRNA), amounts of protein present, nuclear localization of LSF, etc. Such methods may be carried out during one or more of initial diagnosis, during monitoring of treatment, during periodic follow-ups of treatment, or for persons who are determined to be at risk for developing a cancer associated with overexpression and/or over activity of LSF, e.g. persons with a genetic or other predisposition of developing cancer, for example, those whose parents have or had the disease, or in whom occupational hazards result in a risk of cancer. In other embodiments, such testing may be carried out in or for individuals with no known risk factors but simply as a screening procedure to identify individuals with a high likelihood of developing cancer, so that prophylactic measures can be taken.

As will occur to those of ordinary skill in the art, other clinical manifestations, methods of assessing the level of activity/expression of LSF will usually be combined with other assessment techniques, e.g. monitoring of tumor size, of patient health, monitoring metastatic events, etc.

While in one embodiment, the cancer that is detected and treated according to the methods described herein is HCC, this need not always be the case. Correlation of LSF expression (both up-regulation and down-regulation) with other types of cancer are also documented herein, including but not limited to: glioma, meningioma, oligodendroglioma, breast cancer, lung cancer (both adenocarcinoma and squamous cell carcinoma), head and neck squamous cell carcinoma pancreatic, ovarian and thyroid cancers, etc. Any type of cancer that is associated with LSF may be detected, diagnosed, monitored, treated, etc. by the methods described herein.

The present invention also provides compositions for use in treating cancer in an individual in need thereof. The composition may include one or more substantially purified LSF inhibitors as described herein and a pharmacologically suitable carrier. The preparation of such compositions is well known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain auxiliary substances such as wetting or emulsifying agents, pH buffering agents, salts, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of LSF inhibitor in the formulations may vary. However, in general, the amount in the formulations will be from about 1-99%.

The LSF inhibitor compositions (preparations) of the present invention may be administered by any of the many suitable means which are well known to those of skill in the art, including both local and systemic administration. Such means include but not limited to: intravenously, by direct injection into or in the vicinity of a tumor (i.e. intra-tumorally or in close proximity to the tumor); by injection that is not intratumora (e.g. intramuscular); by inhalation; orally; intravaginally or intrarectally, e.g. as a suppository); intranasally; topically; as eye drops; via sprays; etc. In preferred embodiments, the mode of administration is intravenous or intratumoral.

In addition, the compositions may be administered in conjunction with other treatment modalities such as substances that boost the immune system, various other chemotherapeutic agents (e.g. platinum drugs, 5-fluorouracil, doxyrubin, interferon, etc.), antibiotic agents, anti-nausea agents, and the like. Further, administration of LSF inhibitors may be carried out in conjunction with other therapies such as radiation therapy, surgical excision/resection of a tumor or portions of a tumor, etc. All such combinations of therapies are encompassed by the present invention.

The invention also provides methods of identifying compounds which inhibit LSF. Those of skill in the art are familiar with such methods, which typically involve screening large numbers of compounds (e.g. more than about 100; 1000; 10,000 or even more than 100,000; 200,000; 300,000 or more) in a single assay, e.g. using a fluorescence polarization or other assay that detects binding of a compound to LSF, or which detects the inhibition of binding of LSF to one or more of its usual binding sites, e.g. to a DNA binding site. For example, synthetic chemical compounds can be screened for their ability to prevent the binding of LSF to the OPN promoter. Further, those of ordinary skill in the art are familiar with publically available databases which can be accessed and queried in order to identify compounds which have already been screened in vitro, e.g. the databases of the National Cancer Institute (NCI). Such databases include results of the screening of compounds which have the ability to bind to a variety of targets, and/or to impact the growth of various types of cancer cells, etc. Once a suitable target is identified as associated with a particular disease or condition (such as LSF, described herein for the first time as associated with HCC) such a database can be used to identify suitable compounds which bind LSF, prevent its binding to a target of interest (e.g. DNA, such as the promoter regions of OPN), or which are somehow associated with a disease or condition of interest (e.g. HCC). With the knowledge of a suitable target (e.g. LSF) it is well within the purview of one of skill in the art to identify and conduct specific tests of such compounds with respect to their ability to inhibit or lessen the expression or activity of LSF. Further, it is well within the purview of one of ordinary skill in the art to identify closely related compounds, or to design closely related compounds, and to test their efficacy for inhibiting LSF expression or activity.

The invention also provides diagnostic methods related to cancer. Such diagnostic methods may be used, for example, to determine the stage or progress of an occurrence of cancer in an individual; and/or for determining or estimating (predicting) the prognosis of a cancer patient; and/or to guide the development of cancer treatment protocols for a subject (human or animal). Generally, the diagnostic methods involves identifying a patient who has or is suspected of having cancer, and obtaining a sample of tissue that is believed or suspected to be cancerous from the patient, e.g. via a biopsy of a solid tumor. Those of skill in the art are familiar with techniques for obtaining, storing and treating such samples. Once a sample is obtained, an assessment is carried out to determine the level of expression and/or activity and/or potential for expression of LSF. Alternatively, or in addition, the level of expression and/or activity of a molecule in a cancer-related pathway that is controlled or influenced by or associated with LSF is determined. Those of skill in the art will recognize that any of several methodologies may be used to assess LSF expression or activity (and/or that of a molecule from a cancer-related pathway). For example, interrogation of the genome of cells in the sample can elucidate the number of chromosomes, chromosome segments or genes of interest in a tumor cell, to e.g. detect polysomy, polyploidy, etc.; determination of RNA levels (e.g. mRNA) may also be used; determination of peptide or protein levels (e.g. of monomeric or polymeric LSF or fragments thereof using, for example, monoclonal or polyclonal antibodies (e.g. with fluorescent labels); nuclear localization of LSF by immunochemistry, etc.

Once a level and or pattern of expression of LSF (and optionally, at least one other relevant molecule) in a sample has been determined, that level is compared to previously established reference values. Typically, such reference values include expression values from healthy control subjects, i.e. negative controls from subjects who do not have cancer, and also from known samples of cancerous cells or tumors (i.e. positive controls), which may represent e.g. several stages or grades of tumors. Once a comparison to reference values is made, the resulting information may be used in any of several ways, e.g. to determine or confirm the presence or absence of cancer; to establish the stage or grade of cancer; to predict the prognosis for the patient (e.g. whether or not the cancer is readily treatable, the chances of success of treatment, likely lifespan of the patient, etc.); and also to develop suitable treatment strategies. For example, if a patient is determined to have an early stage of aggressive cancer, the full arsenal of treatment options may be employed, including inhibition of LSF, surgery, radiation therapy, etc. Alternatively, if the patient is found to have early stage non-aggressive cancer, less drastic measures may be sufficient to achieve success.

Typically, data from reference samples is stored in a database, and the methods of the invention are implemented using software programs designed and computers configured to implement the methods. Generally, data from an analysis as described herein is used as input for the computer program, which then queries the database and outputs a result or conclusion. Alternatively, or in addition, a skilled practitioner may view and interpret the results. Once a conclusion is made, one or more skilled practitioners may further conclude how to use the information, e.g. to develop treatment protocols or options for treatment protocols The "patients" or "subjects" or "individuals' who are treated or diagnosed by the methods of the invention are generally mammals, and frequently humans. However, this need not always be the case. The methods may be extended to non-mammalian species, and veterinary applications of the technology are also contemplated.

EXAMPLES

Example 1

Hepatocellular carcinoma (HCC) is a highly aggressive cancer with no currently available effective treatment. Understanding the molecular mechanism of HCC development and progression is imperative to develop novel, effective and targeted therapies for this lethal disease. In the present Example, we document that the cellular transcription factor Late SV40 Factor (LSF) plays an important role in HCC pathogenesis.

LSF protein was significantly overexpressed in human HCC cells compared to normal hepatocytes. In 109 HCC patients, LSF protein was overexpressed in >90% cases, compared to normal liver, and LSF expression level showed significant correlation with the stages and grades of the disease. Forced overexpression of LSF in less aggressive HCC cells resulted in highly aggressive, angiogenic and multi-organ metastatic tumors in nude mice. Conversely, inhibition of LSF significantly abrogated growth and metastasis of highly aggressive HCC cells in nude mice. Microarray studies revealed that as a transcription factor, LSF modulated specific genes regulating invasion, angiogenesis, chemoresistance and senescence. The expression of osteopontin (OPN), a gene regulating every step in tumor progression and metastasis, was robustly upregulated by LSF. It was documented that LSF transcriptionally upregulates OPN and loss-of-function studies demonstrated that OPN plays an important role in mediating the oncogenic functions of LSF. Together, these data establish a regulatory role of LSF in cancer, particularly HCC pathogenesis, and validate LSF as a viable target for therapeutic intervention.

Materials and Methods

Cell Lines, Culture Condition, Viability, Colony Formation Assays, Anchorage-Independent Growth in Soft Agar and Matrigel Invasion Assays:

Primary rat hepatocytes were isolated and cultured as described (19). SNU-423 cells were obtained from ATCC and cultured as instructed. HepG3, QGY-7703, Hep3B, HuH7, Focus and HEK-293 cells were cultured as described (20). Cell viability was determined by standard MTT assays as described (5). Colony formation, anchorage-independent growth in soft agar and matrigel invasion assays were performed exactly as described (5).

Tissue Microarray:

Human HCC tissue microarrays were obtained from Imgenex Corp. Two tissue microarrays were used: one containing 40 primary HCC, 10 metastatic HCC and 9 normal adjacent liver samples (Imgenex; IMH-360), the other containing 46 primary HCC and 13 metastatic HCC (Imgenex; IMH-318) for immunohistochemistry. IMH-360 was used for Fluorescence in situ hybridization analysis (FISH).

Construction of Stable Cell Lines:

LSF and dominant negative LSF (LSFdn) expression constructs were described previously (9). HepG3 clones stably expressing LSF and QGY-7703 clones stably expressing LSFdn were created by transfecting the corresponding expression constructs using lipofectamine 2000 (Invitrogen) and selection with neomycin. An empty pcDNA3.1(+)-Neo plasmid was used similarly to establish the control clones. The LSF17 clone of HepG3 cells was transduced with a pool of three to five lentiviral vector plasmids, each encoding target-specific 19-25 nt (plus hairpin) shRNAs designed to knockdown osteopontin (OPN) gene expression (Santa Cruz Biotechnology). Individual colonies were selected by puromycin. Lentiviral particles expressing scrambled shRNA were used to similarly establish LSF-17Consh clones.

Transient Transfection and Luciferase Assay:

Transfection was carried out using lipofectamine 2000 (Invitrogen) according to the manufacturer's protocol. For LSF luciferase reporter assays, cells were plated into 24-well plates and the next day transfected with empty vector (pGL3-basic), pGL3B-WT4-E1b (luciferase reporter plasmid containing four tandem LSF-binding site; LSF WT-Luc) or pGL3B-MT4-E1b (luciferase reporter plasmid containing four tandem mutated LSF-binding site; LST MT-Luc) and renilla luciferase expression plasmid for transfection control (9). For the NF-κB luciferase reporter assay, cells were plated into 24-well plates and the next day transfected with 3κB-luc (luciferase reporter plasmid containing 3 tandem repeats of NF-κB-binding site) and renilla luciferase expression plasmid for transfection control (21). Cells were incubated in the absence or presence of TNF-α (10 ng/ml) for 12 h. For the OPN promoter luciferase assay, cells were transfected with OPN-Prom-Luc construct containing ~1 kb of OPN promoter upstream of the luciferase gene (kindly provided by Dr. Paul C. Kuo, Duke University) along with a renilla luciferase expression plasmid (16). Luciferase assays were measured using a Dual Luciferase Reporter Assay kit (Promega) according to the manufacturer's protocol and firefly luciferase activity was normalized by renilla luciferase activity.

Preparation of Whole Cell Lysates and Western Blot Analyses:

Preparation of whole cell lysates and Western blot analyses were performed as described (5). The primary antibodies used were anti-LSF (1:2,000; mouse monoclonal; BD Biosciences), anti-pERK (1:2,000; rabbit polyclonal; Cell Signaling), anti-ERK (1:2,000; rabbit polyclonal; Cell Signaling), anti-pAKT (1:1,000; rabbit polyclonal; Cell Signaling) and anti-AKT (1:1,000; rabbit polyclonal; Cell Signaling). Blots were stripped and normalized by re-probing with anti-β-tubulin (1:1,000; mouse monoclona; Sigma).

Immunostaining:

Immunofluorescence analysis in tumor sections was performed essentially as described (5). Anti-LSF (1:200; mouse monoclonal; BD Biosciences), anti-Ki-67 (1:200; mouse monoclonal; BD Biosciences) and anti-CD31 (1:200, mouse monoclonal, Dako) antibodies were used. Images were analyzed using an Olympus immunofluorescence microscope. For the tissue microarray (IMH-360 and IMH-318, Imgenex) anti-LSF antibody was used at 1:100 dilution and the signals were developed by avidin-biotin-peroxidase complexes with a DAB substrate solution (Vector laboratories).

Nude Mice Xenograft Studies:

Subcutaneous xenografts were established in the flanks of athymic nude mice using $1 \times 10^6$ human HCC cells and the clones. Tumor volume was measured twice weekly with a caliper and calculated using the formula $\pi/6 \times$ larger diameter$\times$(smaller diameter). Mice were followed for 3 weeks. For the metastasis assays, $1 \times 10^6$ cells were intravenously injected through the tail vein in nude mice. The lungs, intestines, liver, bone and other organs were isolated and analyzed after 4 weeks. All experiments were performed with at least 5 mice in each group and all the experiments were repeated 3 times.

Total RNA Extraction, Real Time PCR and Microarray Assay:

Total RNA was extracted using Qiagen miRNAeasy mini kit (Qiagen). Real time PCR was performed using an ABI 7900 fast real time PCR system and Taqman gene expression assays for OPN, CFH and GAPDH according to the manufacturer's protocol (Applied Biosystems). An Affymetrix oligonucleotide microarray (GeneChip® Human Genome U133A 2.0) analysis was performed to compare gene expression between Control-8 and LSF-17 clones of HepG3 cells using standard Affymetrix® protocol (22).

Fluorescence In Situ Hybridization and Micronuclei Analysis:

Dual color fluorescence in situ hybridization (FISH) was performed as previously described on hepatocellular carcinoma tissue microarrays (23). Bacterial artificial chromosome (BAC)-derived test probes targeting LSF (12q13, RP11-142E3, BACPAC Resources Center) were paired with an enumeration probe for the pericentromeric region of chromosome 12 (D12Z3) for dual-target hybridization. For micronuclei analysis, interphase nuclei from the parental HepG3 cells and LSF-1 clones were harvested and slides prepared according to standard procedures using the criteria of Fenech (24). The frequency of micronuclei present in the cell lines was compared using a Chi-square test using a significance level of $\alpha=0.05$.

Chromatin Immunoprecipitation (ChIP) Assays:

ChIP assays were performed using a commercially available kit from Active Motif (Carlsbad, Calif.) according to the manufacturer's protocol. OPN promoter-specific primers, sense 5' ACACGCTTATGCGGGTATGT 3' (SEQ ID NO: 1)

and antisense 5' GAACATTTGGTAGGGGGAAA 3'(SEQ ID NO: 2) were used. Statistical analysis: Data were represented as the mean±Standard Error of Mean (S.E.M) and analyzed for statistical significance using one-way analysis of variance (ANOVA) followed by Newman-Keuls test as a post hoc test. To assess the strength of association between LSF expression and stages of HCC an ordinal logistic regression was conducted with the stage of HCC as the ordinal response and LSF expression as the independent variable in the proportional odds model using Pearson's chi-square test with Yates' continuity correction.

Results and Discussion

Figure 1A:
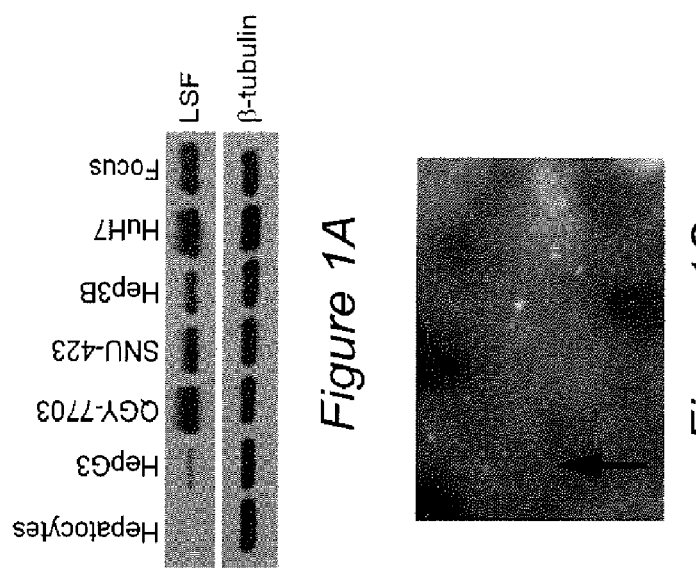

While in normal hepatocytes LSF protein expression was virtually undetected, its expression was robustly upregulated in human HCC cells, except HepG3 cells, which do not form tumors in nude mice (FIG. 1A) (5). These findings were extended by tissue microarrays containing 86 primary HCC, 23 metastatic HCC and 9 normal adjacent liver samples that were immunostained using anti-LSF antibody. Little to no LSF immunostaining was detected in the 9 normal liver samples while significant LSF staining was observed in HCC samples (FIG. 1B). LSF expression was detected predominantly in the nucleus (not shown). Among the 109 HCC samples, only nine scored negative for LSF and the remaining 100 (91.7%) showed variable levels of LSF that could be significantly correlated with the stages of the disease based on the BCLC staging system (Table 1) (12). Expression of LSF gradually increased with the stages from I-IV (FIG. 1B) as well as with the grades of differentiation from well-differentiated to poorly differentiated (e.g., compare panels b and e, panels c and f and panels d and g in FIG. 1B).

TABLE 1

Immunoperoxidase staining of normal liver and different stages of HCC by tissue microarray using anti-LSF antibody*

|  | 0 | + | ++ | +++ | Total cases |
|---|---|---|---|---|---|
| Normal Liver | 4 | 5 |  |  | 9 |
| Stage I HCC | 4 | 15 | 3 | 1 | 23 |
| Stage II HCC | 1 | 14 | 8 | 2 | 25 |
| Stage III HCC | 3 | 15 | 15 | 5 | 38 |
| Stage IV HCC | 1 | 4 | 8 | 10 | 23 |

*To assess the strength of association between LSF expression and stages of HCC, an ordinal logistic regression was conducted with the stage of HCC as the ordinal response and LSF expression as the independent variable in the proportional odds model. The hypothesis of association is highly significant: P value < 0.001 using Pearson's chi-square test with Yates' continuity correction. A total of 109 HCC cases were analyzed.

Figure 1C:
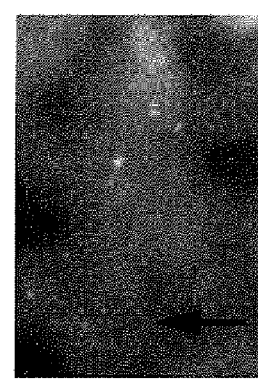

Amplification of chromosome band 12q13, the location of the LSF gene, has been reported in some cases of HCC (13, 14). To examine the possibility that copy number gain might be the underlying mechanism of LSF protein overexpression in human HCC patients, dual color fluorescence in situ hybridization (FISH) was performed on human HCC tissue microarrays containing 9 normal liver samples and 50 HCC samples. Bacterial artificial chromosome (BAC)-derived test probe targeting LSF was used along with a control probe that is specific for the pericentromeric region of chromosome 12 (D12Z3). The control probe (D12Z3) provided information regarding the number of chromosomes 12 present in the cell. Copy number gains of LSF (amplification or low level gain) were not encountered in any of the HCC samples. However, 34 out of 50 HCC samples (68%) exhibited an increased number of signals for both the LSF and D12Z3 probes, suggesting the presence of extra copies of a large region of chromosome 12 or polyploidy. FIG. 1C shows a representative cell (arrow) in which four differentially labeled dots are observed in the original. In the original photograph, red dots represented signals from LSF probe, while green dots represented signals from D12Z3 probe. The presence of four signals from both control (D12Z3) and target (LSF) probes were clearly visible, and indicated that there are four copies of chromosome 12 indicating polysomy. Thus chromosome 12 polysomy might be one mechanism of LSF protein overexpression in human HCC in addition to its regulation by AEG-1.

Figure 2A:
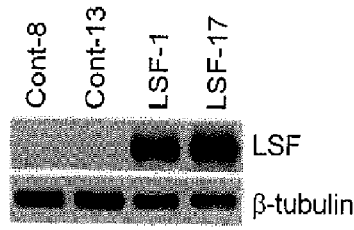
FIGS. 2A-F. LSF overexpression increases proliferation, anchorage-independent growth and invasion of HepG3 cells. A. Control-8 (Cont-8) and Control-13 (Cont-13) clones are neomycin-resistant clones while LSF-1 and LSF-17 clones are LSF-overexpressing clones of HepG3 cells. Western blot analysis was performed to detect LSF and β-tubulin expression in these cells. B. LSF WT-Luc: luciferase reporter plasmid preceded by 4 tandem LSF-binding sites; LSF-MT-Luc: luciferase reporter plasmid preceded by mutated LSF-binding sites. The indicated cells were transfected with either empty pGL3-basic vector or LSF WT-Luc or LSF MT-Luc along with renilla luciferase expression vector. Luciferase assay was performed 2 days later and firefly luciferase activity was normalized by renilla luciferase activity. C. Cell viability of the indicated cells at the indicated time points were measured by standard MTT assay. D. Colony formation assay for the indicated cells. Colony number per 250 cells is shown. E. Soft agar assay for the indicated cells. For D and E, the colonies were scored two weeks after plating. F. Matrigel invasion assay using the indicated clones. The inset represents the invading cells. For B-F: the data represents mean±SEM.
Figure 2B:
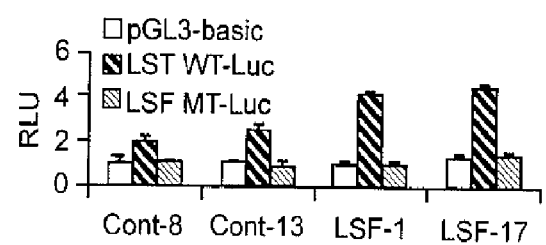
Figure 2C:
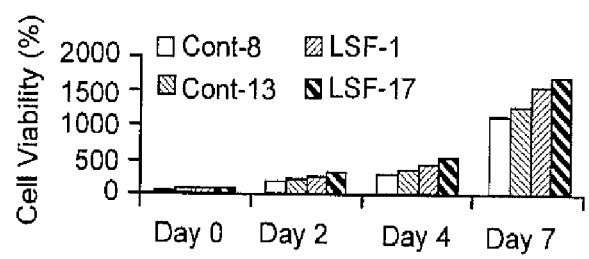
Figure 2D:
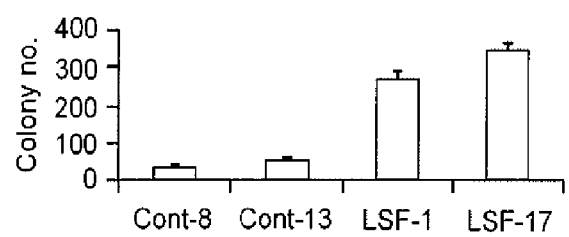
Figure 2E:
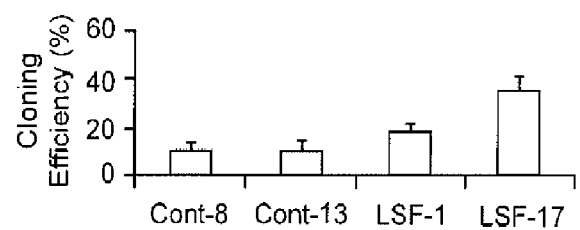
Figure 2F:
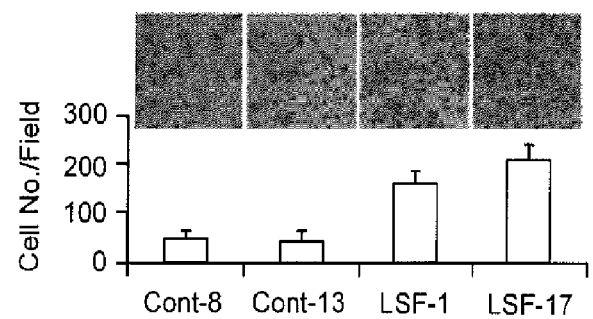

Compared to other HCC cell lines, HepG3 cells express significantly lower level of LSF. To examine the effect of LSF overexpression in HepG3 cells, we established stable cell lines expressing LSF. Several of these clones were analyzed for LSF overexpression, among which LSF-1 and LSF-17 clones showed LSF expression that is comparable to a naturally LSF-overexpressing cell line, such as QGY-7703 (FIG. 2A). The nuclear expression of LSF was confirmed in LSF-17 clone by immunofluorescence (not shown). The luciferase activity of LSF WT-luc, a luciferase reporter construct containing 4 LSF-binding sites, was significantly higher in LSF-1 and LSF-17 clones compared to control neomycin-resistant clones Control-8 and Control-13 (FIG. 2B). Both LSF-1 and LSF-17 clones showed higher proliferative activity (FIG. 2C), colony forming ability (FIG. 2D), anchorage-independent growth in soft agar (FIG. 2E) and matrigel invasion (FIG. 2F) abilities compared to Control-8 and Control-13 clones. Interestingly, LSF overexpression resulted in chromosomal instability in HepG3 cells as evidenced by a significantly increased frequency of micronuclei in the LSF-1 clone ($p<0.05$) (not shown).

Figure 3A:
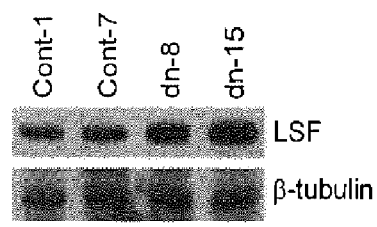
FIGS. 3A-F. Dominant negative LSF (LSFdn) inhibits proliferation, anchorage-independent growth and invasion by QGY-7703 cells. A. Control-1 (Cont-1) and Control-7 (Cont-7) clones are neomycin-resistant clones while LSFdn-8 (dn-8) and LSFdn-15 (dn-15) clones are dominant negative LSF-overexpressing clones of QGY-7703 cells. Western blot analysis was performed to detect LSF and β-tubulin expression in these cells. B. The indicated cells were transfected with either empty pGL3-basic vector or LSF WT-Luc or LSF MT-Luc along with renilla luciferase expression vector. Luciferase assay was performed 2 days later and firefly luciferase activity was normalized by renilla luciferase activity. C. Cell viability of the indicate cells at the indicated time points were measured by standard MTT assay. D. Colony formation assay for the indicated cells. Colony number per 250 cells is shown. E. Soft agar assay for the indicated cells. For D and E, the colonies were scored two weeks after plating. F. Matrigel invasion assay using the indicated clones. The inset represents the invading cells. For B-F: the data represents mean±SEM.
Figure 3B:
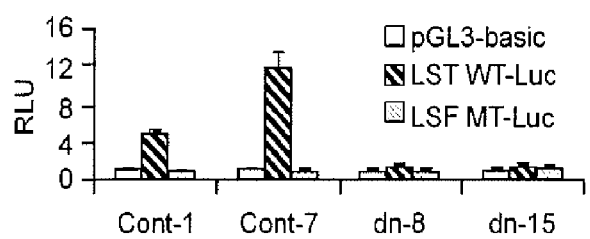
Figure 3C:
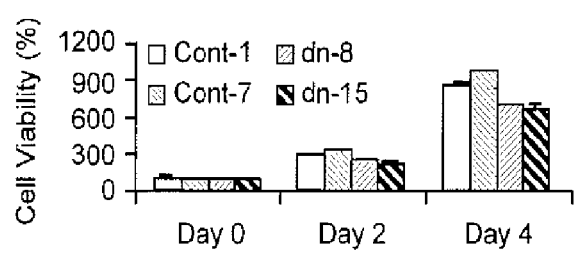
Figure 3D:
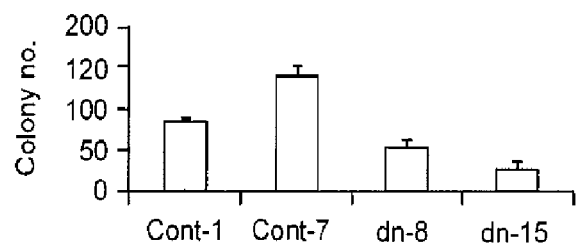
Figure 3E:
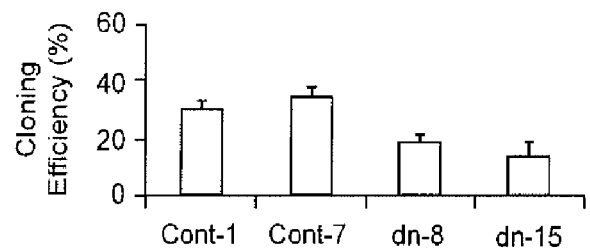
Figure 3F:
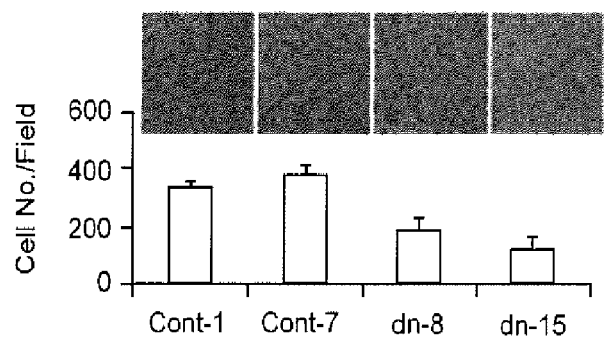

As complementation to the LSF-overexpressing clones, we established stable clones of QGY-7703 cells expressing a dominant negative LSF (LSFdn, a double amino acid substitution mutant of LSF initially named 234QL/236KE that is unable to bind DNA) (9). An increased level of LSF expression over the control clones indicated expression of LSFdn. LSFdn-8 and LSFdn-15 clones expressed significantly higher levels of LSFdn compared to neomycin-resistant control clones Control-1 and Control-7 (FIG. 3A). The authenticity of these clones was confirmed by lack of activity of LSF WT-luc in LSFdn-8 and LSFdn-15 clones compared to Control-1 and Control-7 clones (FIG. 3B). Compared to Control-1 and Control-7 clones, LSFdn-8 and LSFdn-15 clones had a slower proliferation rate (FIG. 3C), and less colony formation (FIG. 3D), anchorage-independent growth in soft agar (FIG. 3E) and matrigel invasion abilities (FIG. 3F).

Figure 4A:
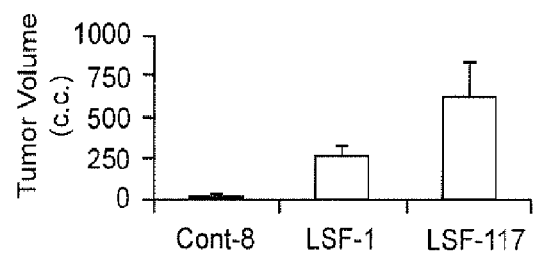
FIGS. 4A-F. Overexpression of LSF increases and inhibition of LSF decreases tumorigenesis of human HCC cells in nude mice. Control-8, LSF-1 and LSF-17 clones of HepG3 cells were subcutaneously implanted in athymic nude mice. Tumor volume (A) and tumor weight (B) were measured 3 weeks after implantation. Control-1, Control-7, LSFdn-8 and LSFdn-15 clones of QGY-7703 cells were subcutaneously implanted in athymic nude mice. Tumor volume (C) and tumor weight (D) were measured 3 weeks after implantation. Immunofluorescence analysis of LSF, Ki-67 and CD31 in tumor sections of LSF-1 and LSF-17 clones of HepG3 cells (E) and Control-7 and LSFdn-15 clones of QGY-7703 cells (F).
Figure 4B:
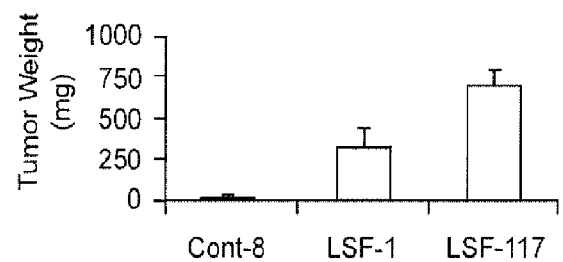
Figure 4C:
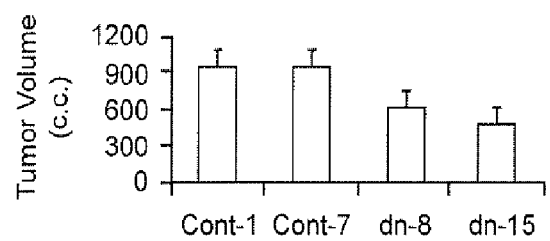
Figure 4D:
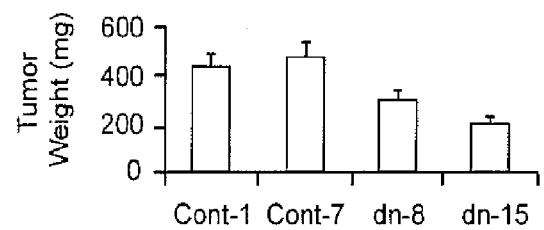
Figure 4E:
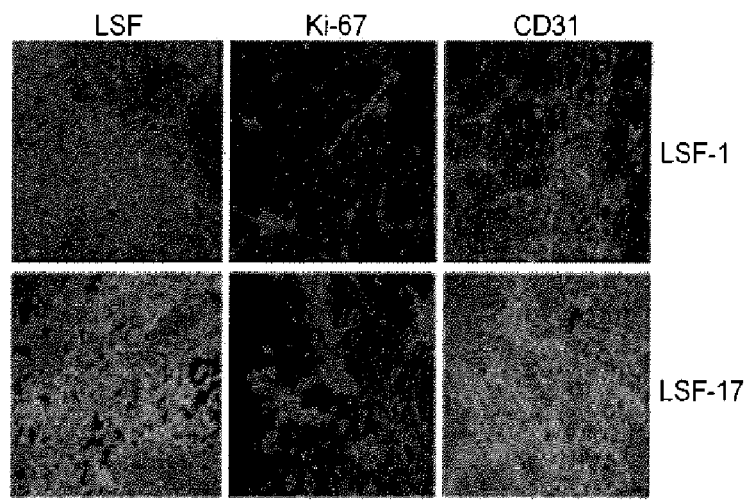
Figure 4F:
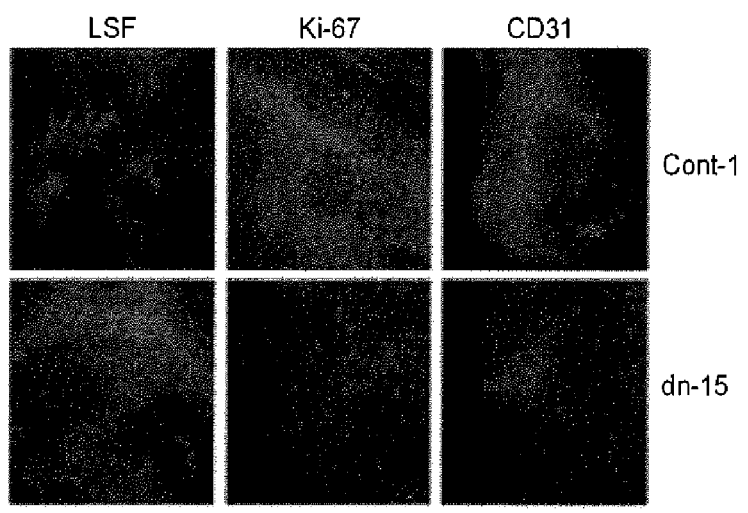

The tumor promoting properties of LSF were confirmed by nude mice xenograft assays. While control HepG3 clone Control-8 did not form any tumors, LSF-1 and LSF-17 clones reproducibly generated large and aggressive tumors when implanted subcutaneously in the flanks of athymic nude mice (FIGS. 4A and 4B). As a corollary, LSFdn-8 and LSFdn-15 clones of QGY-7703 cells formed significantly smaller subcutaneous tumors in nude mice compared to the control QGY-7703 clones, Control-1 and Control-7 (FIGS. 4C and 4D). Analysis of LSF-1 and LSF-17 tumor sections revealed high LSF expression, high proliferation index (analyzed by Ki-67 expression) and increased angiogenesis (determined by CD31 expression indicative of microvessel formation) (FIG. 4E). As expected LSFdn-15 tumors showed high LSFdn expression, low proliferation index (Ki-67 expression) and decreased angiogenesis (CD31 expression) compared to Control-7 tumors (FIG. 4F). These findings indicate that LSF positively regulates growth and invasion of HCC cells.

Figure 5A:
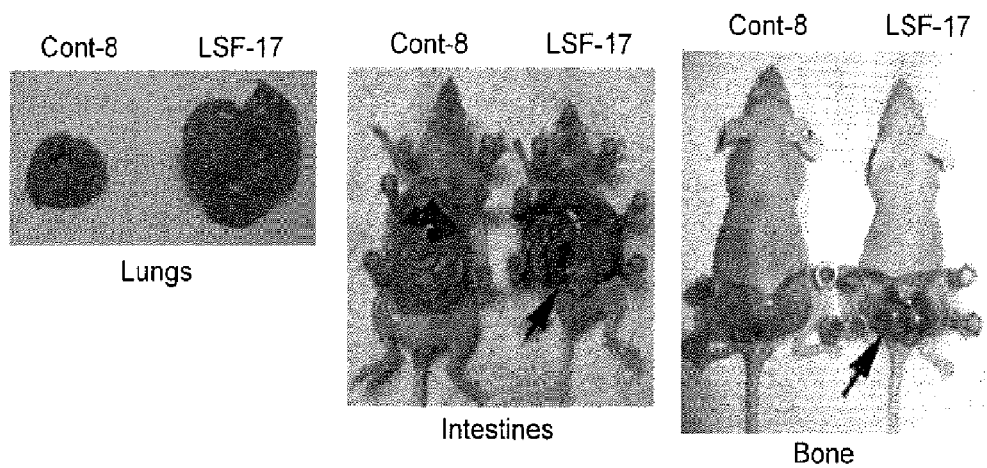
FIGS. 5A-E. Overexpression of LSF increases and inhibition of LSF decreases metastasis of human HCC cells in nude mice. A. Control-8 and LSF-17 clones of HepG3 cells were injected intravenously through the tail vein in athymic nude mice. The internal organs were analyzed 4-6 weeks after injection. B. Kaplan-meier survival curve of animals injected with either Control-8 or LSF-17 clones of HepG3 cells. Asterisk (*) represents mice losing ~20% body weight and euthanized (considered as dead). C. Control-1 and LSFdn-15 clones of QGY-7703 cells were injected intravenously through the tail vein in athymic nude mice. Metastatic tumors were visible externally in mice injected with the Control-1 clone but not with the LSFdn-15 clone. D. Graphical representation of metastatic lung nodules in the animals injected with Control-8 and LSF-17 clones of HepG3 cells. Inset shows H&E sections of lungs. E. Graphical representation of metastatic lung nodules in the animals injected with Control-1 and LSFdn-15 clones of QGY-7703 cells. Inset shows H&E sections of lungs. For D and E, The data represent mean±SEM.
Figure 5B:
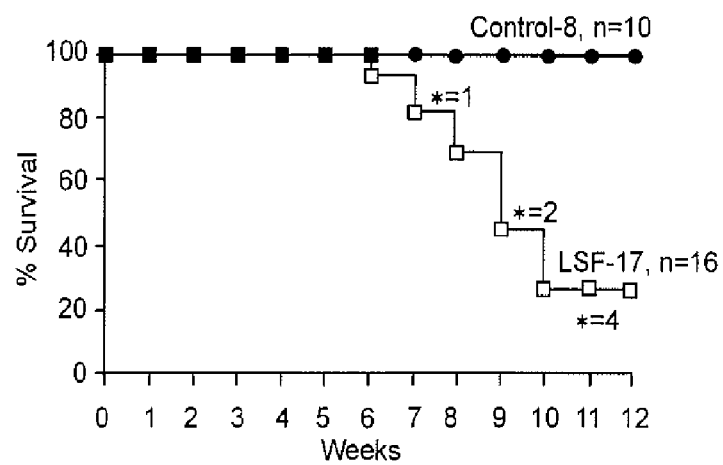

In in vitro assays the most significant effect of LSF overexpression or inhibition was observed in the matrigel invasion assay (FIGS. 1 and 3). Since invasion is the first step in metastasis, we evaluated the metastasizing capabilities of the established clones by the tail vein metastasis assay. Intravenous injection of LSF-1 and LSF-17 clones (figures shown only for LSF-17 clone) resulted in multi-organ macrometastasis while no metastasis was observed for Control-8 clone of HepG3 cells (FIG. 5A). Metastasis was observed in the lungs (FIG. 5A, left panel), intestinal regions (FIG. 5A, middle panel; arrow) and liver and in the lower back region involving the vertebral column (FIG. 5A, right panel; arrow). The LSF-17-injected animals lost significant body weight (compare the size of the animals in FIG. 5A middle and right panels), became cachexic, and started losing ~20% body weight (indication for euthanasia and considered as dead) 6 weeks after injection (FIG. 5B). As demonstrated by Kaplan-Meier survival curves, 80% of the animals injected with LSF-17 clone died by 12 weeks after injection, while none of the animals injected with the Control-8 clone of HepG3 cells died (FIG. 5B). Staining of the lungs showed preservation of normal alveolar architecture in Control-8 injected animals while in LSF-17-injected animals the lungs were filled with a solid mass of infiltrating tumor cells adjacent to the blood vessels indicating that the tumor cells had extravasated, lodged into the lungs and established colonies (FIG. 5D).

Figure 5C:
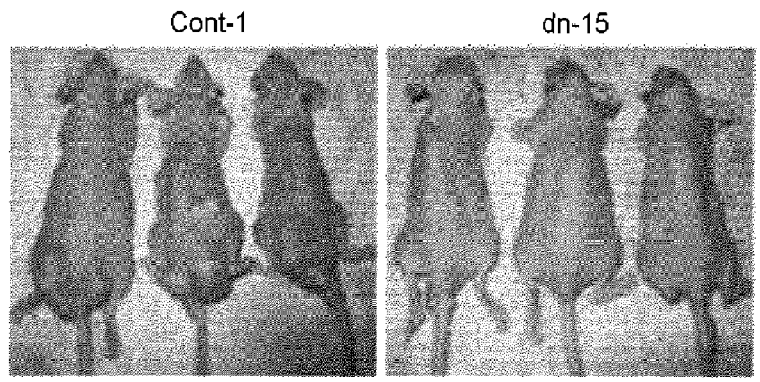
Figure 5D:
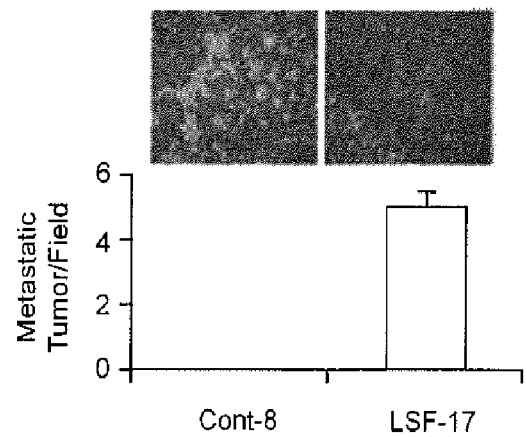
Figure 5E:
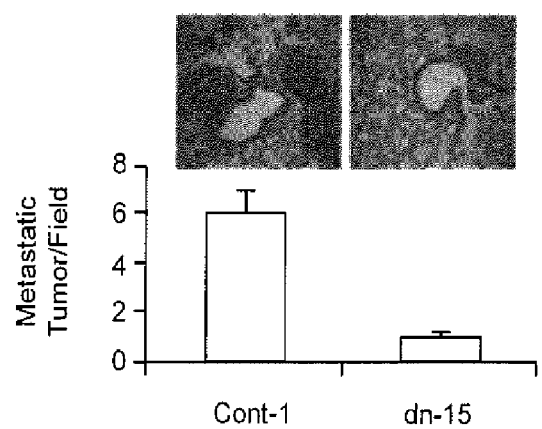

For QGY-7703 cells the Control-1 and Control-7 clones gave rise to multi-organ metastatic tumors while LSFdn-8 and LSFdn-15 clones did not show any external signs of metastasis (FIG. 5C). Staining of the lungs identified multiple solid nodules in Control-1-injected animals while normal architecture was preserved in LSFdn-15-injected animals, with only a few isolated metastatic nodules (FIG. 5E).

Figure 6A:
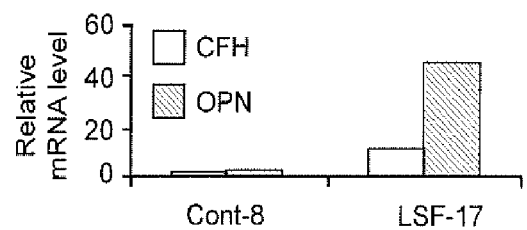
FIGS. 6A-F. Osteopontin (OPN) expression is transcriptionally induced by LSF. A. Real-time PCR analysis of CFH and OPN mRNA expression in Control-8 and LSF-17 clones of HepG3 cells (A) and Control-1 and LSFdn-15 clones of QGY-7703 cells (B). C. OPN expression was detected by ELISA in Control-8 and LSF-17 clones of HepG3 cells (left panel) and Control-1 and LSFdn-15 clones of QGY-7703 cells (right panel). D. Schematic diagram of OPN promoter-luciferase construct showing the location of LSF-binding sites in the promoter and primers designed for ChIP assay. E. Control-8 and LSF-17 clones of HepG3 cells were transfected with pGL3-basic vector or OPN-Prom-luc along with renilla luciferase expression vector. Luciferase assay was performed 2 days later and firefly luciferase activity was normalized by renilla luciferase activity. F. Chromatin Immunoprecipitation (ChIP) assay to detect LSF binding to the OPN promoter.
Figure 6B:
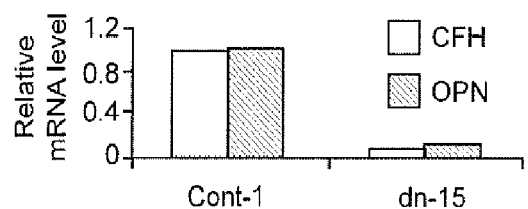
Figure 6C:
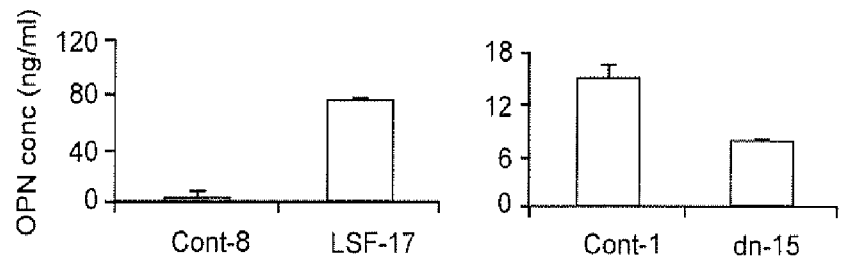
Figure 6D:
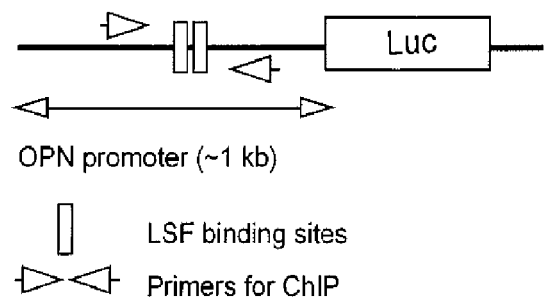
Figure 6E:
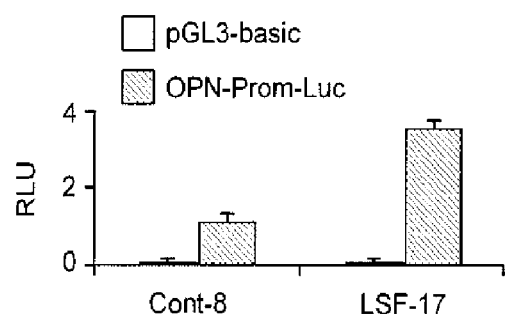
Figure 6F:
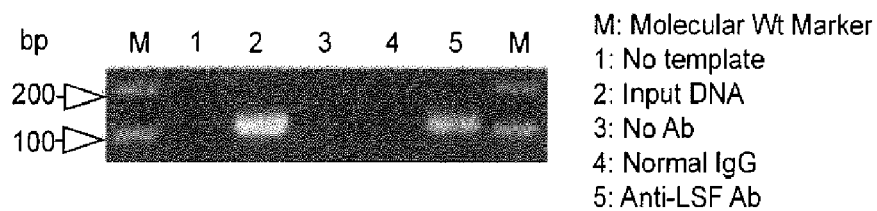

To identify the downstream genes mediating the effects of LSF in HCC cells, gene expression profiles were compared between Control-8 and LSF-17 clones of HepG3 cells by Affymetrix microarray (GEO accession #GSE19815). With a 2.0 fold cut-off, expression levels of 125 genes were upregulated while those of 148 genes were downregulated upon overexpression of LSF. Twenty-one (21) of these genes are directly involved in the process of tumorigenesis (Table 2). The most robust induction was observed for SPP1, which encodes osteopontin (OPN), known to be important for regulating every step in metastasis (15). The microarray data were confirmed by quantitative RT-PCR for several genes, showing ~40-fold increase in OPN mRNA expression in the LSF-17 clone, as compared to the Control-8 clone (FIG. 6A). As a corollary, OPN mRNA expression was markedly downregulated in the LSFdn-15 clone of QGY-7703 cells compared to the Control-1 clone (FIG. 6B). Another LSF-downstream gene, complement factor H (CFH) also showed a similar trend (FIGS. 6A and 6B). These findings were confirmed at the protein level by ELISA (FIG. 6C). The robust induction of OPN in LSF-overexpressing clones prompted us to hypothesize that LSF might regulate OPN expression at the transcriptional level. We scanned ~1 kb region of the OPN promoter and identified two tandem LSF binding sites in this region. Consistent with that prediction, OPN promoter-luciferase reporter construct demonstrated significantly higher activity in the LSF17 clone compared to the Control-8 clone (FIG. 6E) (16). Finally, a chromatin Immunoprecipitation (ChIP) assay confirmed LSF binding to the OPN promoter (FIG. 6F).

TABLE 2

Tumor-associated genes regulated by LSF identified by microarray.

| Probe Set | Gene ID | Direction | Function | Fold-change* | p-value** | q-value |
|---|---|---|---|---|---|---|
| 209875_s_at | SPP1 | Up | Invasion and metastasis | 16.4 | 7.23E−07 | 5.04E−04 |
| 203824_at | TSPAN8 | Up | Invasion and metastasis | 10.5 | 4.35E−07 | 3.9E−04 |
| 200872_at | S100A10 | Up | Invasion and metastasis | 7.4 | 1.26E−05 | 1.08E−03 |
| 209847_at | CDH17 | Up | Invasion and metastasis | 4.6 | 7.15E−08 | 1.40E−04 |
| 202668_at | EFNB2 | Up | Angiogenesis | 2.3 | 3.20E−04 | 3.16E−03 |
| 212764_at | ZEB1 | Up | EMT and invasion | 2.0 | 1.14E−03 | 6.00E−03 |
| 209752_at | REG1A | Up | Growth and regeneration | 5.2 | 1.05E−06 | 5.53E−04 |
| 205815_at | REG3A | Up | Growth and regeneration | 3.4 | 2.442E−04 | 2.75E−03 |
| 207096_at | SAA4 | Up | Acute phase protein | 2.3 | 3.58E−04 | 3.26E−03 |
| 205547_s_at | TAGLN | Down | Inhibitor of MMP9 | 5.7 | 8.39E−06 | 1.01E−03 |
| 215388_s_at | CFH | Up | Complement inhibitor | 4.2 | 8.32E−05 | 1.89E−03 |
| 203638_s_at | FGFR2 | Up | Cell growth | 2.5 | 1.57E−05 | 1.10E−03 |
| 201983_s_at | EGFR | Up | Cell growth | 2.0 | 2.37E−05 | 1.23E−03 |
| 206754_s_at | CYP2B7P1 | Up | Drug metabolism | 9.2 | 4.55E−06 | 7.86E−04 |
| 206755_at | CYP2B6 | Up | Drug metabolism | 6.7 | 6.53E−06 | 9.39E−04 |
| 202831_at | GPX2 | Up | Drag metabolism | 5.1 | 3.87E−06 | 7.86E−04 |
| 204646_at | DPYD | Up | Drug metabolism | 2.0 | 2.36E−04 | 2.72E−03 |
| 210451_at | PKLR | Up | Glycolysis | 2.0 | 6.69E−04 | 4.54E−03 |
| 221558_s_at | LEF1 | Up | Wnt signaling | 2.1 | 8.87E−05 | 1.92E−03 |

TABLE 2-continued

Tumor-associated genes regulated by LSF identified by microarray.

| Probe Set | Gene ID | Direction | Function | Fold-change* | p-value** | q-value |
|---|---|---|---|---|---|---|
| 213620_s_at | ICAM2 | Up | Cell adhesion (NFκB downstream) | 2.2 | 1.58E−04 | 2.35E−03 |
| 201163_s_at | IGFBP7 | Down | Senescence | 3.9 | 2.47E−04 | 2.79E−03 |

*LSF-17/Control-8
**p-value represents statistical significance, q-value represents false discovery rate (FDR).

Figure 7A:
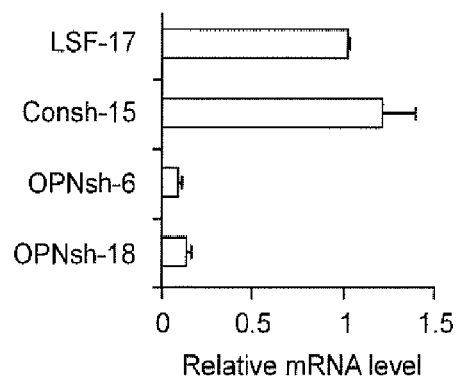
FIGS. 7A-F. Inhibition of OPN abrogates augmentation of proliferation, anchorage-independent growth and invasion by LSF. LSF-17-OPNsh-6 (OPNsh-6) and LSF-17-OPNsh-18 (OPNsh-18) clones stably express OPN shRNA and were generated in the background of LSF-17 clone of HepG3 cells. LSF-17consh-15 (Consh-15) clone stably expresses control scrambled shRNA and was also generated in LSF-17 background. A. OPN mRNA expression detected by real-time PCR in the indicated clones. B. OPN protein expression detected by ELISA in the indicated clones. C. Cell viability of the indicated cells at the indicated time points were measured by standard MTT assay. D. Colony formation assay for the indicated cells. E. Soft agar assay for the indicated cells. F. Matrigel invasion assay of the indicated clones. The data represents mean±SEM.
Figure 7B:
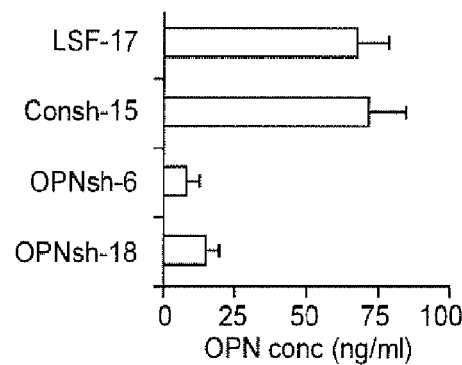
Figure 7C:
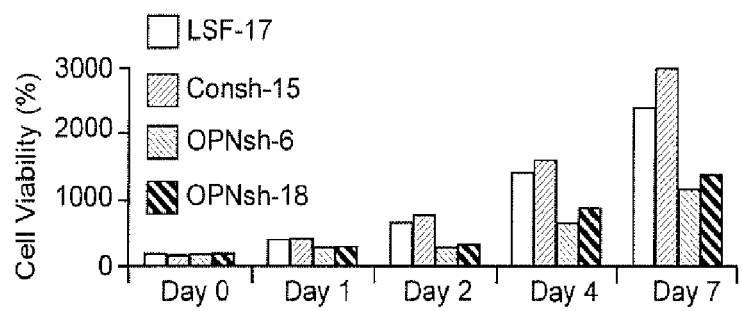
Figure 7D:
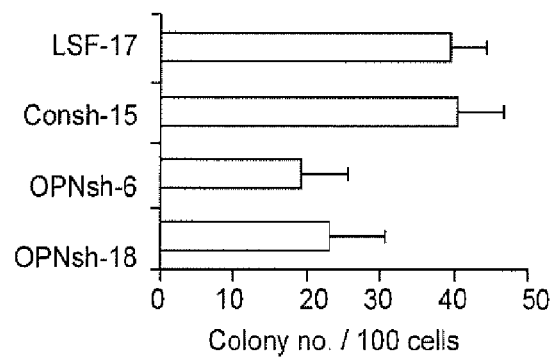
Figure 7E:
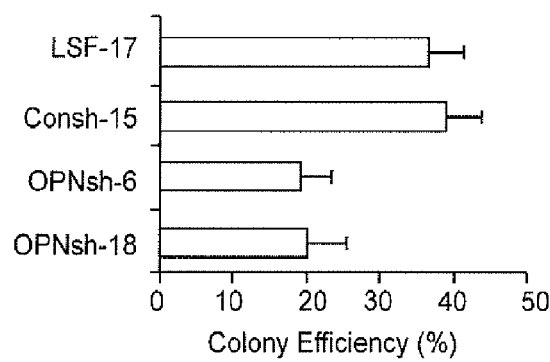
Figure 7F:
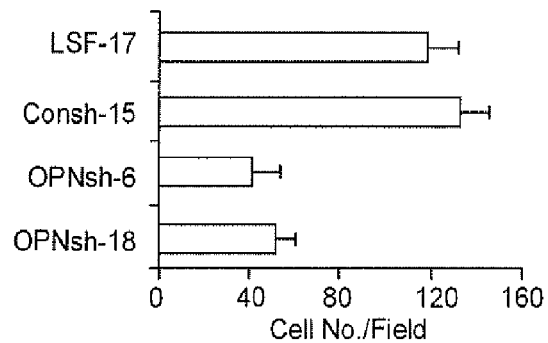
Figure 8A:
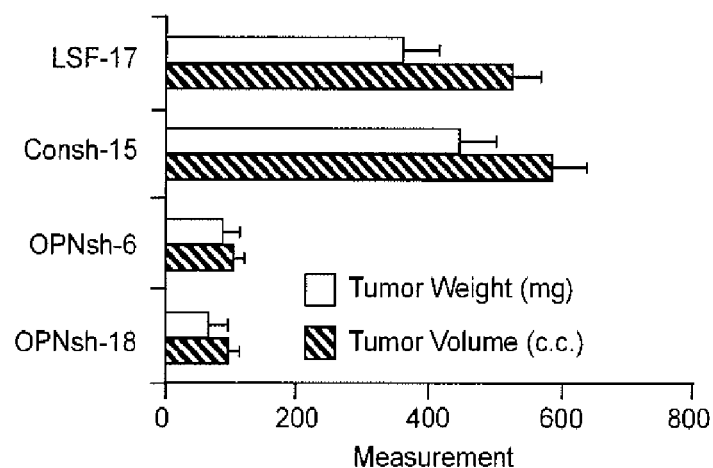
FIGS. 8A-D. Inhibition of OPN abrogates LSF-induced tumorigenesis and metastasis. The indicated clones were subcutaneously implanted in athymic nude mice. A. Tumor volume and tumor weight were measured 3 weeks after implantation. B. Graphical representation of metastatic lung nodules in the animals injected with the LSF-17consh-15 and LSF-17-OPNsh-18 clones via tail vein. The data represent mean±SEM. Inset: H&E sections of lungs of animals injected with the indicated clones. C. Parental HepG3 cells were treated with conditioned media from Control-8 or LSF-17 clone of HepG3 cells and then subjected to matrigel invasion. D. Matrigel invasion assay using LSF17 clone of HepG3 cells in the presence of neutralizing antibodies. Integrin: anti-αvβ3 integrin antibody. CD44: anti-CD44 antibody. The data represent mean±SEM.
Figure 8B:
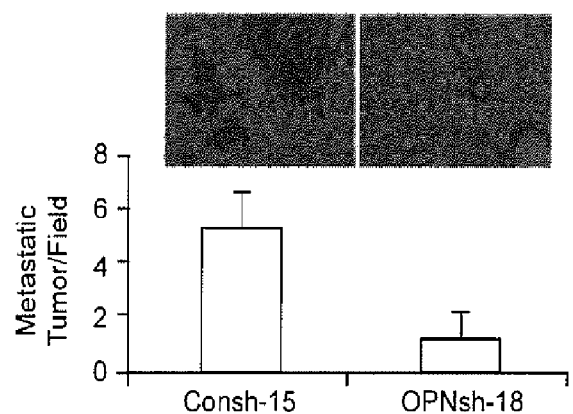

To confirm the role of OPN in mediating LSF's effect, we established stable OPN shRNA expressing clones in the background of LSF-17 clone of HepG3 cells (LSF17-OPNsh). Two independent clones LSF-17-OPNsh-6 and LSF-17-OPNsh-18 showed marked downregulation of OPN mRNA and protein expression (FIGS. 7A and 7B, respectively) when compared to the parental LSF-17 clone or LSF-17consh-15 clone that stably expresses control scrambled shRNA. LSF expression remained unchanged in LSF-17, LSF-17consh-15 and LSF-17-OPNsh clones (not shown). Compared to parental LSF-17 and LSF-17consh-15 clone, LSF17-OPNsh-6 and LSF17-OPNsh-18 clones had a significantly slower proliferation rate (FIG. 7C), and less colony formation (FIG. 7D), anchorage-independent growth in soft agar (FIG. 7E) and matrigel invasion abilities (FIG. 7F). LSF17-OPNsh-6 and LSF17-OPNsh-18 clones formed significantly smaller subcutaneous tumors in nude mice compared to the parental LSF-17 and LSF-17consh-15 clone (FIG. 8A). These studies were further corroborated by experimental metastasis assays demonstrating a significantly decreased number of metastatic nodules in the lungs of mice injected with LSF17-OPNsh-18 clone compared with those injected with LSF-17consh-15 clone (FIG. 8B).

Figure 8C:
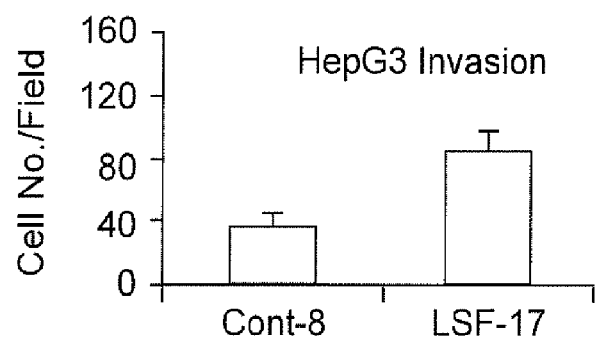
Figure 8D:
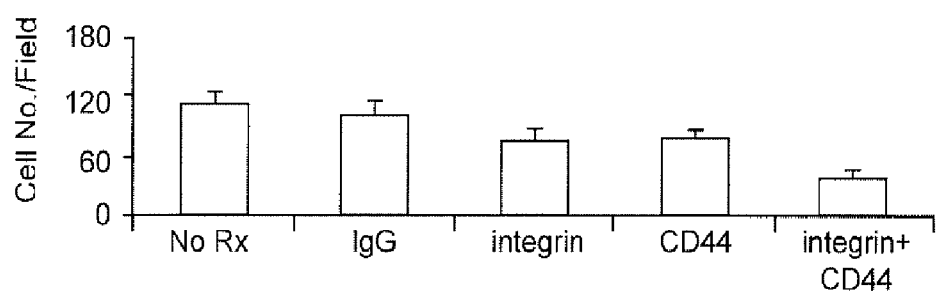

Since OPN is a secreted protein, we checked whether conditioned media from LSF-17 clones might augment the invasive ability of the parental HepG3 cells. Indeed, conditioned media from the LSF-17 clone, but not from the Control-8 clone, significantly increased invasion by HepG3 cells (FIG. 8C). OPN works through αvβ3 integrin and CD44 receptors (15). We blocked these receptors in the LSF17 clone of HepG3 cells with neutralizing antibodies and performed the matrigel invasion assay. While normal IgG did not affect the invasive ability of the LSF17 cells, anti-αvβ3 integrin or anti-CD44 antibody significantly inhibited invasion while the combination of the two antibodies decreased the invasion even further, confirming that OPN working through its canonical receptors plays a key role in regulating LSF function (FIG. 8D). It should be noted that for all the assays described in this manuscript using isolated clones, similar in vitro phenotypes, although less pronounced because of transfection efficiency, were observed with transient transfection assays without selection, thereby ruling out any clonal bias arising from the selection procedure.

These findings reveal a novel role of LSF in the process of hepatocarcinogenesis. We demonstrate that by augmenting transcription of OPN, LSF promotes aggressive progression of HCC. OPN levels can thus be used as a sensitive and specific marker in predicting disease progression in diverse cancers, including HCC, and OPN is known to promote every step in metastasis as well as growth of the primary tumor (15, 17). By regulating OPN expression, LSF functions as a key regulator of HCC development and progression. In addition, LSF also activates two important cell survival regulating pathways, MEKIERK and NF-κB (not shown) and inhibition of the MEK/ERK pathway significantly abrogates invasion by LSF-17 cells (not shown). Activation of NF-κB by LSF suggests its potential role in regulating the inflammatory aspects of HCC (18).

Figure 16:
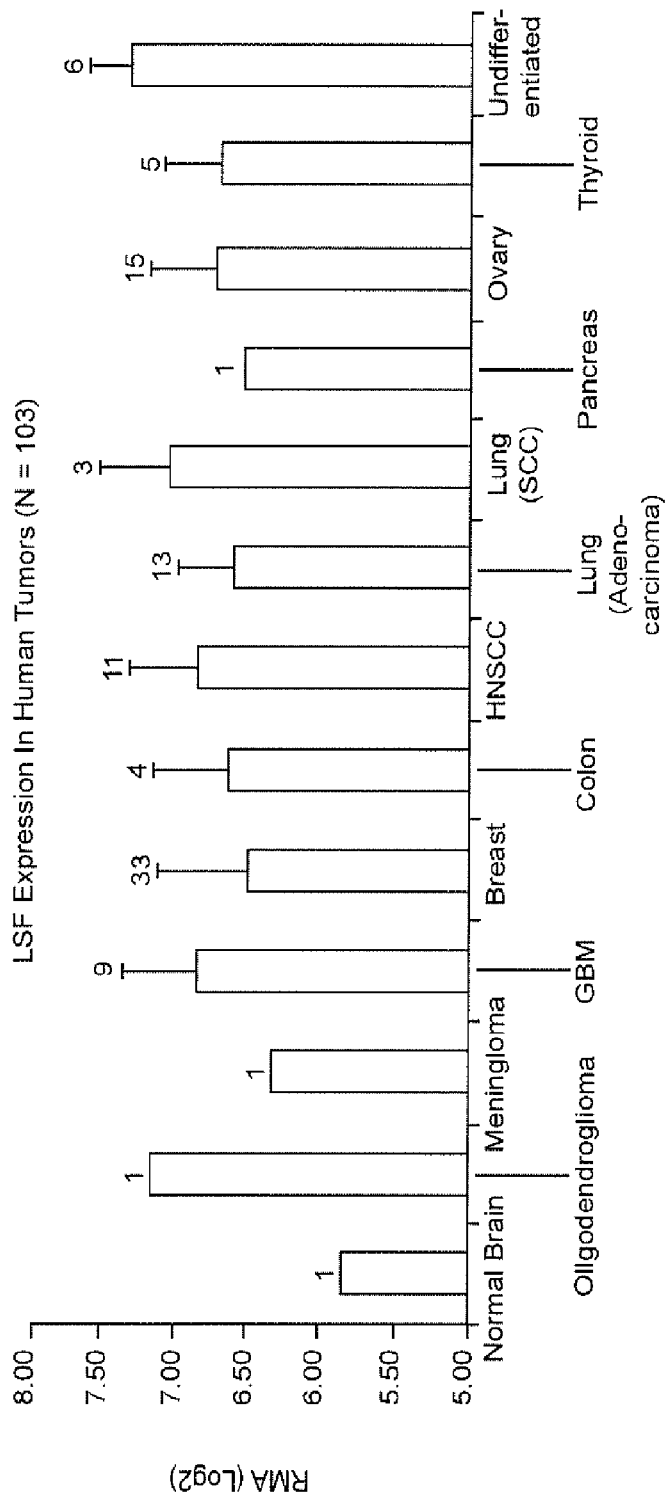
FIG. 16. LSF expression in human tumors; N=103. GBM glioblastoma multiforme; HNSCC=head and neck squamous cell carcinoma; SCC=squamous cell carcinoma.

The findings herein show that LSF is a viable target for the treatment of cancers such as HCC. For example, small or large molecule inhibitors targeting the DNA binding domains of LSF should be effective HCC therapeutics. Additionally, the correlation of LSF expression with the stages and grades of HCC permits the use of LSF as a prognostic marker for this disease. Finally, the observation that LSF is overexpressed in cancer indications other than HCC indicates a potential oncogenic function of LSF in diverse other cancers (FIG. 16).

REFERENCES FOR INTRODUCTION AND EXAMPLE 1

1. El-Serag H B & Rudolph K L (2007) Hepatocellular carcinoma: epidemiology and molecular carcinogenesis. Gastroenterology 132: 2557-2576.
2. Jemal A, et al. (2008) Cancer statistics, 2008. CA: Cancer J Clin 58: 71-96.
3. Parkin D M, Bray F, Ferlay J, & Pisani P (2005) Global cancer statistics, 2002. CA: Cancer J Clin 55: 74-108.
4. Bruix J & Sherman M (2005) Management of hepatocellular carcinoma. Hepatology 42: 1208-1236.
5. Yoo B K, et al. (2009) Astrocyte elevated gene-1 regulates hepatocellular carcinoma development and progression. J Clin Invest 119: 465-477.
6. Yoo B K, et al. (2009) Identification of genes conferring resistance to 5-fluorouracil. Proc Natl Acad Sci USA 106: 12938-12943.
7. Veljkovic J & Hansen U (2004) Lineage-specific and ubiquitous biological roles of the mammalian transcription factor LSF. Gene 343: 23-40.
8. Hansen U, Owens L, & Saxena U H (2009) Transcription factors LSF and E2Fs: tandem cyclists driving G0 to S? Cell cycle 8: 2146-2151.
9. Powell C M, Rudge T L, Zhu Q, Johnson L F, & Hansen U (2000) Inhibition of the mammalian transcription factor LSF induces S-phase-dependent apoptosis by downregulating thymidylate synthase expression. Embo J 19: 4665-4675.
10. Huang J H & Liao W S (1999) Synergistic induction of mouse serum amyloid A3 promoter by the inflammatory mediators IL-1 and IL-6. J Interferon Cytokine Res 19: 1403-1411.
11. Bing Z, Huang J H, & Liao W S (2000) NFkappa B interacts with serum amyloid A3 enhancer factor to synergistically activate mouse serum amyloid A3 gene transcription. J Biol Chem 275: 31616-31623.
12. Llovet J M, Bru C, & Bruix J (1999) Prognosis of hepatocellular carcinoma: the BCLC staging classification. Seminars in liver disease 19: 329-338.

13. Zondervan P E, et al. (2000) Molecular cytogenetic evaluation of virus-associated and non-viral hepatocellular carcinoma: analysis of 26 carcinomas and 12 concurrent dysplasias. J Pathol 192: 207-215.
14. Wilkens L, et al. (2000) Cytogenetic aberrations in primary and recurrent fibrolamellar hepatocellular carcinoma detected by comparative genomic hybridization. Am J Clin Pathol 114: 867-874.
15. Bellahcene A, Castronovo V, Ogbureke K U, Fisher L W, & Fedarko N S (2008) Small integrin-binding ligand N-linked glycoproteins (SIBLINGs): multifunctional proteins in cancer. Nature Rev 8: 212-226.
16. Takami Y, et al. (2007) Sp1 regulates osteopontin expression in SW480 human colon adenocarcinoma cells. Surgery 142: 163-169.
17. Pan H W, et al. (2003) Overexpression of osteopontin is associated with intrahepatic metastasis, early recurrence, and poorer prognosis of surgically resected hepatocellular carcinoma. Cancer 98: 119-127.
18. Pikarsky E, et al. (2004) NF-kappaB functions as a tumour promoter in inflammation-associated cancer. Nature 431: 461-466.
19. Bissell D M & Guzelian P S (1980) Phenotypic stability of adult rat hepatocytes in primary monolayer culture. Ann NY Acad Sci 349:85-98.
20. Su Z Z, Luo Z Y, Guo L P, Li J Z, & Liu Y L (1988) Inhibitory effect of parvovirus H-1 on cultured human tumour cells or transformed cells. Scientia Sinica 31: 69-80.
21. Sarkar D, et al. (2008) Molecular basis of nuclear factor-kappaB activation by astrocyte elevated gene-1. Cancer Res 68: 1478-1484.
22. Irizarry R A, et al. (2003) Summaries of Affymetrix GeneChip probe level data. Nucleic Acids Res 31: e15.
23. Fuller C E, Wang H, Zhang W, Fuller G N, & Perry A (2002) High-throughput molecular profiling of high-grade astrocytomas: the utility of fluorescence in situ hybridization on tissue microarrays (TMA-FISH). J Neuropathol Exp Neurol 61: 1078-1084.
24. Fenech M (2006) Cytokinesis-block micronucleus assay evolves into a "cytome" assay of chromosomal instability, mitotic dysfunction and cell death. Mutat Res 600: 58-66.

Example 2 c-Met Activation Through a Novel Pathway Involving Osteopontin Mediates Oncogenesis by the Transcription Factor LSF Summary:

Understanding the molecular pathogenesis of hepatocellular carcinoma (HCC) would facilitate development of targeted and effective therapies for this fatal disease. The data presented in Example 1 demonstrates that the cellular transcription factor Late SV40 Factor (LSF) is overexpressed in more than 90% of human HCC cases, compared to normal liver, and plays a seminal role in hepatocarcinogenesis. LSF transcriptionally upregulates osteopontin (OPN) that plays a significant role in mediating the oncogenic function of LSF. The present Example describes experiments which further elucidate LSF function by analyzing the signaling pathway modulated by LSF.

Phospho-receptor tyrosine kinase (RTK) array analysis was performed to identify which receptor tyrosine kinases are activated by LSF. Immunohistochemical analysis using tissue microarray was performed to establish correlation among LSF, OPN and phospho-c-Met levels in HCC patients. Co-immunoprecipitation analysis was performed to check OPN-induced CD44 and c-Met interaction. Inhibition studies using chemicals and siRNAs were performed in vitro and in vivo using nude mice xenograft models to establish the importance of c-Met activation in mediating LSF function. The results showed that secreted OPN, induced by LSF, activates c-Met via a potential interaction between OPN and its cell surface receptor CD44. A significant correlation was observed among LSF, OPN and activated c-Met levels in HCC patients. Chemical or genetic inhibition of c-Met resulted in profound abrogation of LSF-mediated tumorigenesis and metastasis in nude mice xenograft studies. These findings thus elucidate a novel pathway of c-Met activation during hepatocarcinogenesis and support the rationale of using c-Met inhibitors as HCC therapeutics.

Background

Hepatocellular carcinoma (HCC) is a major global health problem [1]. The incidence of HCC is increasing in the West, and it is now the third highest cause of cancer-related death globally [1]. In most cases HCC is diagnosed at an advanced stage and has a dismal prognosis owing to the inherent resistance of the disease to conventional anti-cancer therapies [2]. No systemic therapy has improved survival in patients with advanced HCC. In these contexts, defining the molecular determinants of HCC pathogenesis is necessary to develop rationally based targeted and potentially effective therapies for this fatal disease. Our efforts to identify novel regulators of hepatocarcinogenesis revealed overexpression of the transcription factor Late SV40 Factor (LSF) in human HCC cell lines and in more than 90% cases of human HCC, compared to normal hepatocytes and liver, respectively [3] (these observations are set forth in detail in Example 1 above). LSF expression level correlated with the stages and grades of HCC indicating that LSF might be a new prognostic marker for HCC. Stable overexpression of LSF induced a highly aggressive, angiogenic and multi-organ metastatic phenotype in the non-tumorigenic human HCC cell line HepG3 [3]. Conversely, stable dominant-negative inhibition of LSF profoundly abrogated tumor growth and metastasis by a highly aggressive human HCC cell line QGY-7703 [3]. Microarray analysis identified a plethora of genes modulated by LSF including those associated with proliferation, invasion, angiogenesis, metastasis and chemoresistance [3]. Osteopontin (OPN), which is implicated in augmenting every step in tumor progression and metastasis, was found to be the most robustly LSF-induced gene in HCC [3, 4]. We demonstrated that LSF transcriptionally upregulated OPN by directly binding to its promoter and stable shRNA-mediated knockdown of OPN profoundly inhibited oncogenic properties of LSF [3] (these results being discussed in Example 1). We also documented that by transcriptionally regulating thymidylate synthase, LSF contributes to 5-fluorouracil resistance [5]. Thus LSF contributes to an important hallmark of aggressive cancers, i.e., chemoresistance.

c-Met receptor tyrosine kinase (RTK), a cell surface receptor for hepatocyte growth factor (HGF), conveys a unique combination of pro-migratory, anti-apoptotic and mitogenic signals [6-8]. When activated, c-Met initiates epithelial-mesenchymal transition (EMT) by facilitating cell scattering, thereby facilitating migration and invasive growth [7]. c-Met activation has been documented in a variety of cancers and can be induced by gene amplification, transcriptional upregulation, ligand-dependent autocrine or paracrine mechanisms, mutational activation or cross-talk with other RTKs [6, 9]. c-Met plays a pivotal role in HCC that was confirmed by the observation that conditional overexpression of wild-type c-Met in hepatocytes of transgenic mice (an experimental condition that mimics the spontaneous amplification of the c-Met gene observed in human tumors) is sufficient to cause hepatocellular carcinoma that regress following transgene inactivation [10]. Binding of HGF to c-Met leads to autophosphorylation of c-Met in Y1234 and Y1235 residues in the catalytic domain followed by phosphorylation at Y1349 and Y1356 that is essential for recruitment of adaptor proteins [6]. In the absence of ligand, c-Met can be activated by integrin-interaction during cell adhesion, the hyaluronan receptor CD44 and interaction with other RTKs such EGFR or Ron kinase [6, 11, 12]. c-Met activation leads to activation of several pro-survival signaling pathways, such as MEK/ERK and PI3K/Akt pathways, and molecules important for migration, invasion and metastasis, such as Src, STAT3 and the Rho-like GTPase Rac1 [6, 9]. Inhibition of c-Met by blocking antibodies or small molecule inhibitors are being evaluated in Phase I/II clinical trials as potential anti-cancer strategies in diverse cancers [13]. In the present study we document that LSF overexpression activates c-Met. In experiments employing 'gain-of-function' and 'loss-of-function' approaches we document that secreted OPN, induced by LSF, activates c-Met by interaction with CD44. c-Met activation is an important contributor to LSF-mediated oncogenesis.

Materials and Methods

Cell lines and culture condition: Human HCC cell lines HepG3 and QGY-7703 were cultured as described [14]. HepG3 clones stably expressing LSF (LSF-1 and LSF-17) and QGY-7703 clones stably expressing LSFdn (QGY-LSFdn-8 and QGY-LSFdn-15) were generated as described [3] (see also, Example 1 above). LSF-17-Consh-15, LSF-17-OPNsh-6 and LSF-17-OPNsh-18 clones were generated as described [3]. The LSF-17 clone of HepG3 cells was transduced with a pool of three to five lentiviral vector plasmids, each encoding target-specific 19-25 nt (plus hairpin) shRNAs designed to knockdown c-Met gene expression (Santa Cruz Biotechnology). Individual colonies were selected by puromycin for two weeks to generate LSF-17-shMet-1 and LSF-17-shMet-17 clones.

Tissue microarray and human HCC samples: Human HCC tissue microarray (Imgenex; IMH-360) containing 40 primary HCC, 10 metastatic HCC and 9 normal adjacent liver samples was obtained from Imgenex Corp. Patient samples were obtained from the Liver Tissue Cell Distribution System (LTCDS), a National Institutes of Health (NIH) service contract to provide human liver and isolated hepatocytes from regional centers for distribution to scientific investigators throughout the United States (NIH contract N01-DK-7-0004/HHSN267200700004C). The 18 matched nounal liver and HCC sample include LTCDS #1100, 1107, 1135, 1143, 1153, 1154, 1164, 1169, 1172, 1174, 1194, 1216, 1237, 1246, 1260, 1264, 1276 and 1282.

Results

LSF Activates c-Met

HepG3 is a human HCC cell line that is poorly aggressive, non-tumorigenic in nude mice and expresses low level of LSF [14]. In contrast, QGY-7703 is a highly aggressive, metastatic human HCC cell line that expresses high levels of LSF [14]. We established stable cell lines overexpressing LSF in HepG3 background (LSF-1 and LSF-17) and documented that these clones form highly aggressive, multi-organ metastatic tumors in nude mice [3] (see Example 1 above). Conversely, we established stable cell lines expressing an LSF dominant negative mutant in a QGY-7703 background (LSFdn-8 and LSFdn-15) that resulted in profound inhibition of tumor growth and metastasis in nude mice when compared to control clones [3] (see Example 1 above).

Figure 9A:
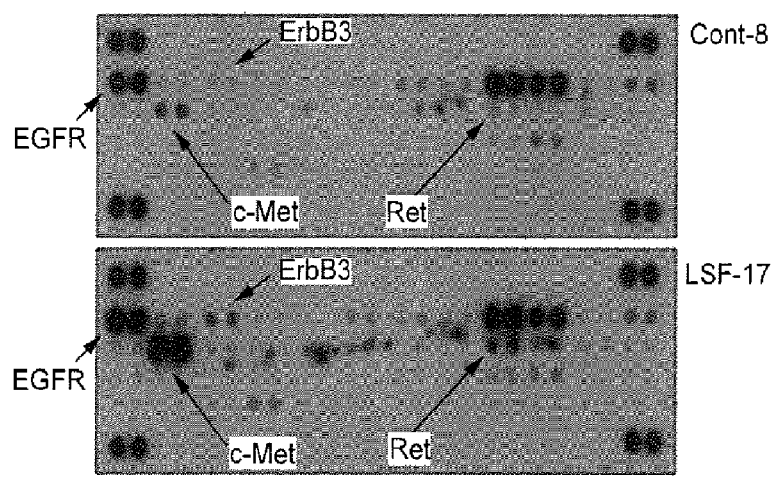
FIGS. 9A-D. LSF activates c-Met. A. Lysates from Control-8 and LSF-17 clones of HepG3 cells were used to detect activated receptor tyrosine kinases (RTKs) using a Proteome Profiler™ Array kit. B. Control-8 (Cont-8) is a neomycin-resistant clone while LSF-1 and LSF-17 clones are LSF-overexpressing clones of HepG3 cells. Control-7 (Cont-7) is a neomycin-resistant clone, while LSFdn-8 (dn-8) and LSFdn-15 (dn-15) clones are dominant negative LSF-overexpressing clones of QGY-7703 cells. Western blot analysis was performed to detect the expression of the indicated proteins in these cells. C. Expression of LSF and p-c-Met was determined by immunohistochemical analysis in FFPE sections of normal liver and matched HCC. A representative figure is shown from one patient. D. Statistical correlation between LSF and phospho-c-Met levels in 50 human HCC patients was analyzed by Pearson's test.
Figure 9B:
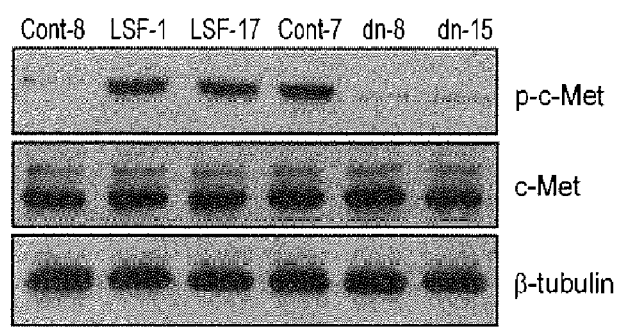
Figure 9C:
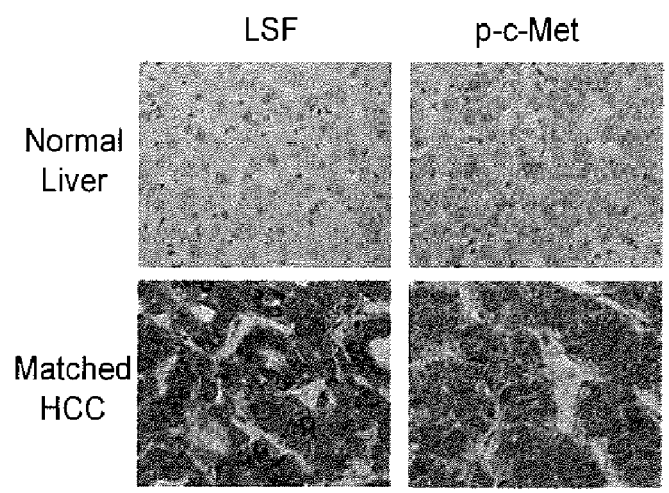
Figure 9D:
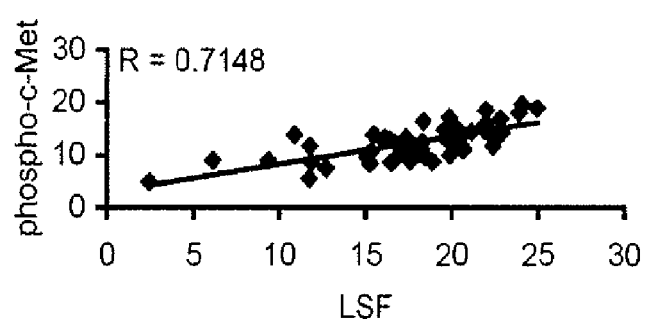

Since LSF modulates multiple signaling pathways in cells, profoundly modulates global gene expression profiles and induces marked phenotypic changes in HCC cells, we hypothesized that LSF might activate receptor tyrosine kinases (RTKs) that induce these profound changes. For this purpose, we used a human phospho-RTK array kit to detect relative levels of tyrosine phosphorylation of human RTKs induced by LSF. We used lysates from Control-8 (control neomycin-resistant clone) and LSF-17 clones of HepG3 cells for this assay. A robust increase in c-Met, a moderate increase in Ret and a small increase in ErbB3 and EGFR activation were observed in the LSF-17 clone as compared to the Control-8 clone (FIG. 9A). Since c-Met showed the most profound activation we investigated the molecular mechanism underlying this phenomenon. The level of activated (phosphorylated) c-Met was significantly higher in LSF-1 and LSF-17 clones compared to the Control-8 clone of HepG3 cells. Similarly, activated c-Met was significantly downregulated in LSFdn-8 and LSFdn-15 clones, compared to the Control-7 clone of QGY-7703 cells (FIG. 9B). The level of total c-Met did not change in either group. We compared LSF and phospho-c-Met levels in normal liver and matched HCC from 18 patients by immunohistochemical analysis. Thirteen of these patients showed increased expression of LSF as well as phospho-c-Met in HCC compared to normal liver. A representative result from one patient is shown in FIG. 9C. These findings were extended by immunohistochemistry in a tissue microarray containing 50 human HCC samples. A statistically significant correlation (R=0.7148) was observed between LSF and phospho-c-Met levels in these patients establishing the link between LSF and c-Met activation in the clinical situation (FIG. 9D).

OPN Mediates LSF-Induced c-Met Activation

Figure 10A:
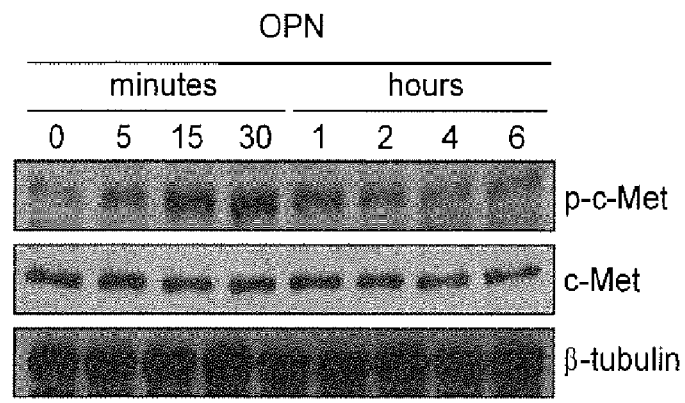
FIGS. 10A-D. OPN activates c-Met. A. HepG3 cells were treated with OPN (100 ng/ml) for the indicated time points and p-c-Met and total c-Met levels were analyzed by Western blot analysis. B. Expression of OPN and p-c-Met was determined by immunohistochemical analysis in FFPE sections of normal liver and matched HCC. A representative figure is shown from one patient. C. Statistical correlation between OPN and phospho-c-Met levels in 50 human HCC patients analyzed by Pearson's test. D. Left panel: LSF-17consh-15 (Consh-15) is a clone of LSF-17 cells that stably expresses control scrambled shRNA and LSF-17-OPNsh-6 (OPNsh-6) and LSF-17-OPNsh-18 (OPNsh-18) are clones of LSF-17 cells stably expressing OPN shRNA. The expression of the indicated proteins was detected by Western blot analysis. Right panel, LSF-17 clone of HepG3 cells were treated with normal IgG (mouse and rabbit; Santa Cruz), anti-αvβ3 integrin antibody (mouse; Millipore) or anti-CD44 antibody (rabbit; Santa Cruz) at a concentration of 20 µg/ml for 24 h and the expression of the indicated proteins was detected by Western blot analysis.
Figure 10B:
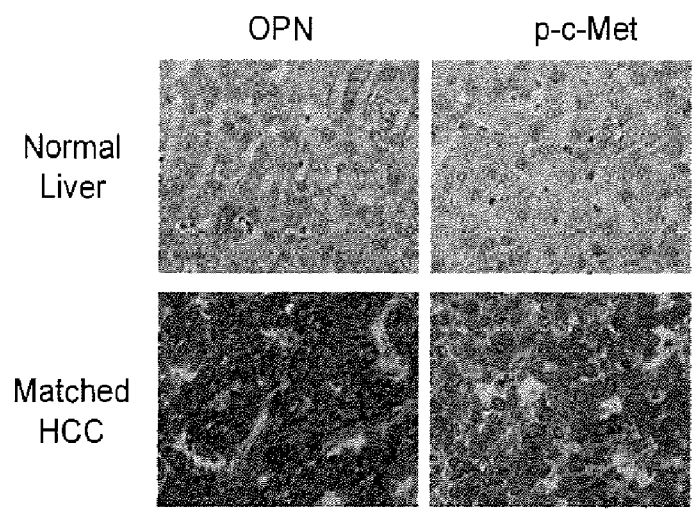
Figure 10C:
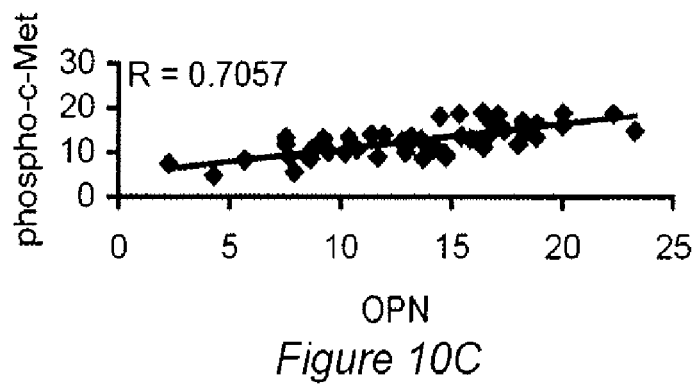

The observation that total c-Met level did not change either by LSF overexpression or inhibition indicates that induction of transcription of c-Met by LSF may not be the probable mechanism of activation of c-Met. We, therefore, explored alternative mechanism(s) of c-Met activation by LSF. Since the most common mechanism of c-Met activation is binding of its ligand HGF, we reasoned that LSF might induce high HGF levels resulting in c-Met activation. However, LSF expression did not result in increased HGF expression level indicating that c-Met activation by LSF occurred independent of HGF. LSF robustly induced the expression of OPN at the transcriptional level and we hypothesized that secreted OPN might result in c-Met activation. Treatment of HepG3 cells with purified OPN resulted in temporal activation of c-Met, which reached the peak level at 30 min post-treatment and then gradually declined although even at 6 h post-treatment the activated c-Met level remained higher than basal level (FIG. 10A). Total c-Met level did not change upon OPN treatment. We compared OPN and phospho-c-Met levels in normal liver and matched HCC from 18 patients by immunohistochemical analysis. Thirteen of these patients showed increased expression of OPN as well as phospho-c-Met in HCC compared to normal liver. A representative result from one patient is shown in FIG. 10B. Statistically significant correlation (R=0.7057) was observed between OPN and phospho-c-Met levels by immunohistochemistry of a tissue microarray of 50 human HCC samples, thereby confirming the link between OPN and c-Met activation in a clinical context (FIG. 10C).

Figure 10D:
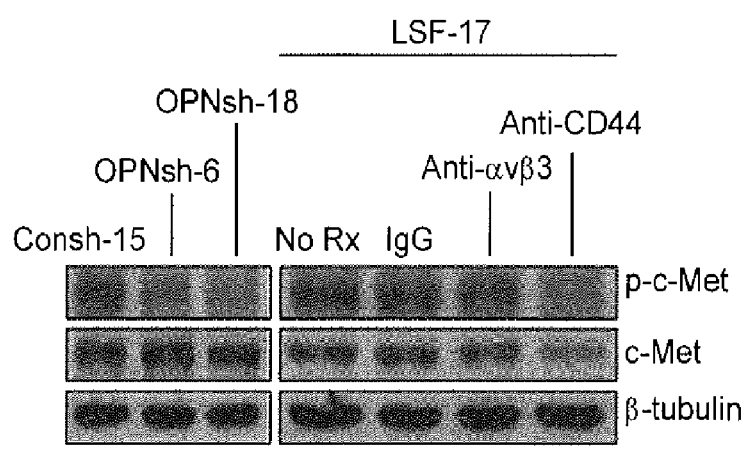

To further confirm the involvement of OPN in mediating LSF-induced c-Met activation, we analyzed activated c-Met levels in stable clones of LSF-17 cells expressing OPN shRNA. These clones have been extensively characterized by us previously [3] (see Example 1 above). Compared to LSF- 17-Consh-15 clone (LSF-17 clone stably expressing control scrambled shRNA), c-Met activation was significantly downregulated in LSF-17-OPNsh-6 and LSF-17-OPNsh-18 clones without affecting total c-Met level (FIG. 10D). OPN works through αvβ3 integrin and CD44 receptors. We blocked these receptors using neutralizing antibodies and analyzed c-Met activation in the LSF-17 clone of HepG3 cells. Blockage of CD44, but not αvβ3 integrin, inhibited c-Met activation indicating that OPN-CD44 interactions mediate c-Met activation (FIG. 10D). CD44 blocking also resulted in a decrease in total c-Met level indicating that inhibition of CD44 and c-Met interaction might result in increased internalization and degradation of c-Met.

OPN Binding to CD44 Mediates c-Met Activation

Figure 11A:
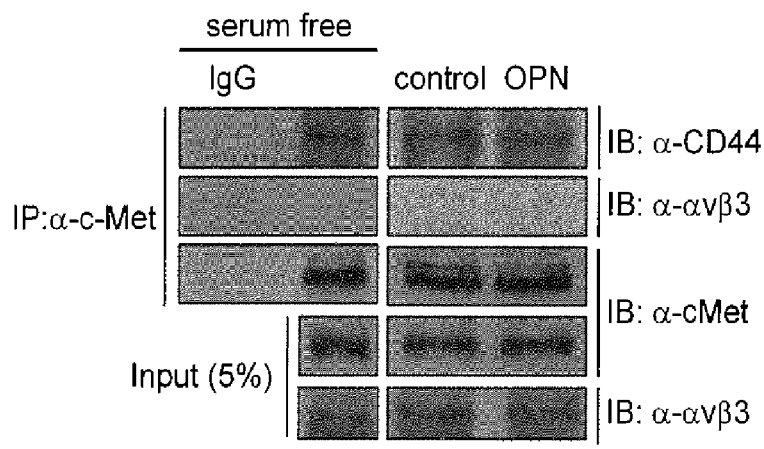
FIGS. 11A-E. OPN facilitates c-Met activation via CD44 receptor. A. Left panel, HepG3 cells were cultured in serum-free conditions. Right panel, HepG3 cells were cultured in serum-containing medium and untreated or treated with OPN (100 ng/ml) for 24 h. Cell lysates were subjected to immunoprecipitation by anti-c-Met antibody and immunoblotting with anti-CD44, anti-αvΘ3 integrin and anti-c-Met antibodies. B. The culture conditions are the same as in A. Immunoprecipitation was done with anti-CD44 antibody and immunoblotting was done with anti-c-Met and anti-CD44 antibody. C. HepG3 cell were cultured in serum-free conditions and then untreated or treated with OPN (100 ng/ml) for 24 h. Immunoprecipitation was done with anti-CD44 antibody and immunoblotting was done with anti-p-c-Met or anti-CD44 antibodies. D. Lysates from LSF-17 and QGY-7703 cells were subjected to immunoprecipitation by anti-c-Met antibody and immunoblotting by anti-CD44, anti-αvβ3 integrin and anti-c-Met antibodies. E. Lysates from LSF-17 and QGY-7703 cells were subjected to immunoprecipitation by anti-CD44 antibody and immunoblotting by anti-c-Met, anti-p-c-Met and anti-CD44 antibodies. The bottom panel serves as inputs for D and E. IgG was used as a control in all the experiments.
Figure 11B:
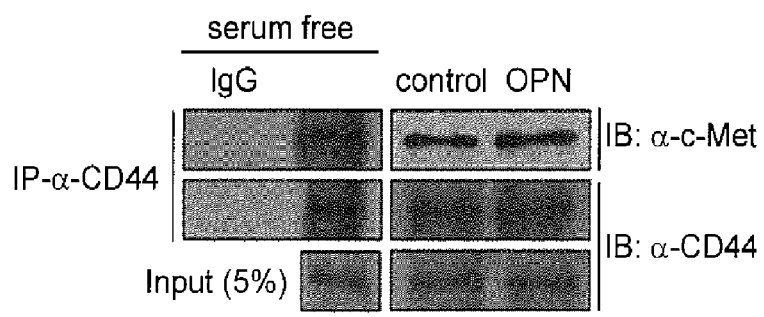
Figure 11C:
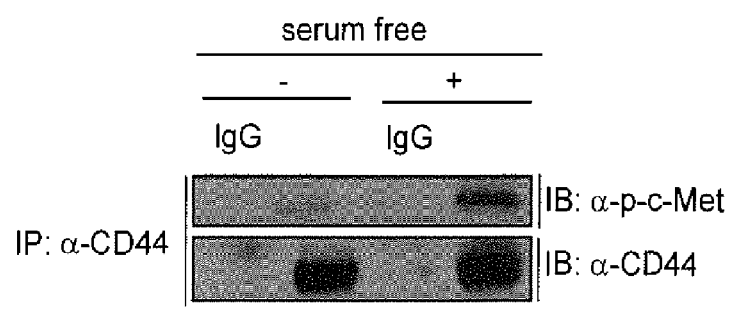
Figure 11D:
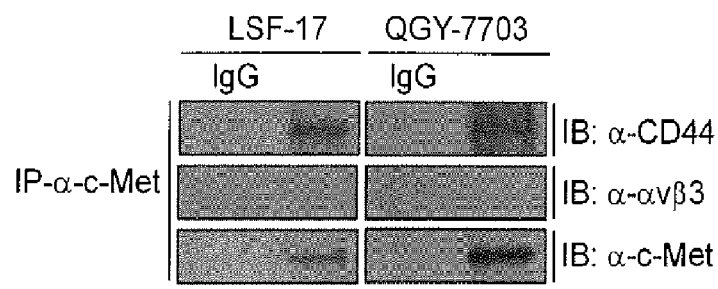
Figure 11E:
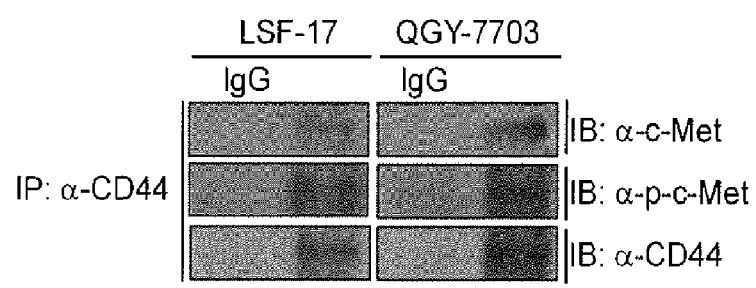
Figure 11E:
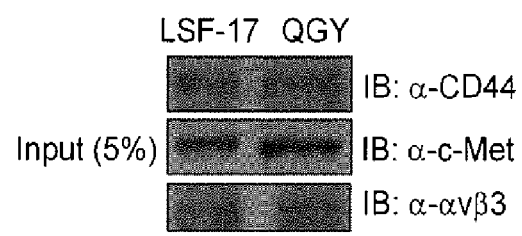

We next explored the molecular mechanism of c-Met activation by OPN using co-immunoprecipitation analysis. Using lysates from HepG3 cells cultured in the absence of serum, anti-c-Met antibody could effectively immunoprecipitate both c-Met and CD44, but not αvβ3 integrin (FIG. 11A, left panel). In serum-containing culture conditions, anti-c-Met antibody immunoprecipitated CD44 and addition of OPN (100 ng/ml) did not affect the binding affinity between c-Met and CD44 (FIG. 11A, right panel). Conversely, under serum-free conditions in HepG3 cells anti-CD44 antibody effectively pulled down both CD44 and c-Met (FIG. 11B, left panel). In serum-containing conditions, the presence or absence of OPN did not affect the binding affinity between CD44 and c-Met. We reasoned that c-Met and CD44 might interact with each other, however, binding of OPN to CD44 might induce a conformational change leading to increased phosphorylation and activation of c-Met. Indeed, under serum-free conditions, treatment of HepG3 cells with OPN significantly increased the association between CD44 and phospho-c-Met (FIG. 11C). These findings were confirmed using LSF-17 clone of HepG3 cells and QGY-7703 cells (that endogenously express high LSF). Anti-c-Met antibody immunoprecipitated both c-Met and CD44, and not αvβ3 integrin, in both cells (FIG. 11D). Conversely, anti-CD44 antibody immunoprecipitated both c-Met and phospho-c-Met (FIG. 11E). These findings indicate that binding of OPN to CD44 might lead to phosphorylation and activation of c-Met.

Figure 12A:
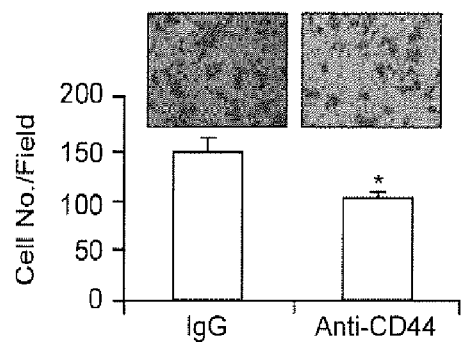
FIGS. 12A-F. Inhibition of CD44 and c-Met by SU11274 blocks LSF function. A. LSF-17 cells were treated with normal IgG or anti-CD44 antibody and then subjected to Matrigel invasion assay. (B, C) Cell viability (MTT) assay of LSF-17 (B) and QGY-7703 (C) cells treated with SU11274 (5 µM) for the indicated time period. (D, E) Matrigel invasion assays of LSF-17 (D) and QGY-7703 (E) cells treated with SU11274 (5 µM). For SU11274 removal, cells were treated with SU11274 for 24 h before seeding them in the invasion chamber in SU11274-free condition. For A-E, data represent mean±SEM. F. HepG3 cells were untreated or treated with OPN (100 ng/ml) and with SU11274 (5 µM) for 24 h and the expression of the indicated proteins were detected by Western blot analysis. Asterisk (*) represents statistically significant difference (p<0.05).

To confirm the involvement of CD44 in mediating LSF function, we treated LSF-17 cells with anti-CD44 blocking antibody and analyzed Matrigel invasion. Anti-CD44 antibody resulted in significant inhibition of invasion by LSF-17 cells in comparison to the isotype control antibody indicating that CD44 is involved in mediating functional activity of LSF (FIG. 12A).

c-Met Plays an Important Role in Mediating LSF Function

Figure 12B:
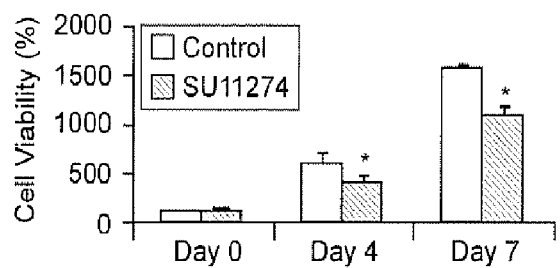
Figure 12C:
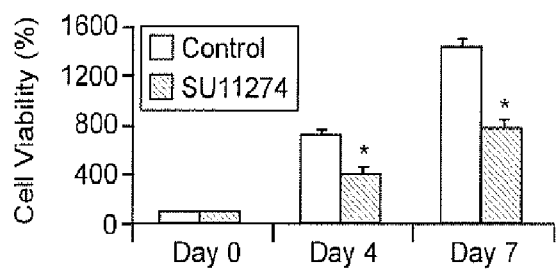
Figure 12D:
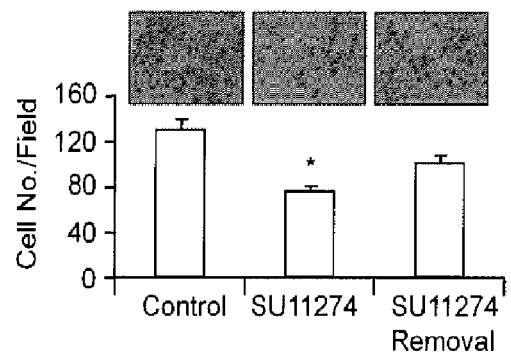
Figure 12E:
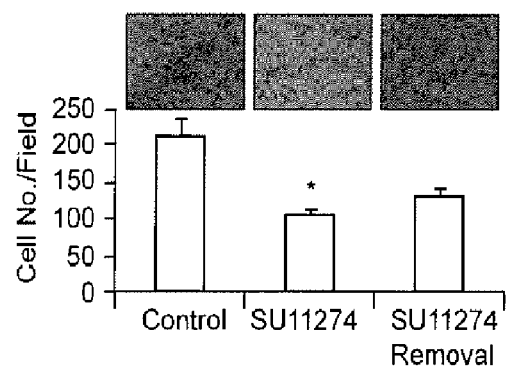

We next investigated the importance of c-Met activation in mediating LSF function. LSF-17 cells and QGY-7703 cells were treated with the chemical inhibitor of c-Met, SU11274 (5 μM), and cell viability and Matrigel invasion was monitored. In both cell lines, cell viability, measured by standard MTT assay, was significantly decreased by SU11274 (FIGS. 12B and 12C, respectively). Similarly, Matrigel invasion by both LSF-17 and QGY-7703 cells was significantly inhibited by SU11274 (FIGS. 12D and 12E, respectively). For invasion assay cells were treated with SU11274 for 24 h, a time point when no significant effect on cell viability was observed. Removal of SU11274 during the invasion assay significantly rescued the cells from inhibition of invasion indicating that persistent inhibition of c-Met activation is obligatory to block LSF-induced augmentation of invasion (FIGS. 12D and 12E, respectively). It should be noted that SU11274 treatment did not affect the viability of the parental HepG3 cells that express low levels of phospho-c-Met (data not shown).

Figure 12F:
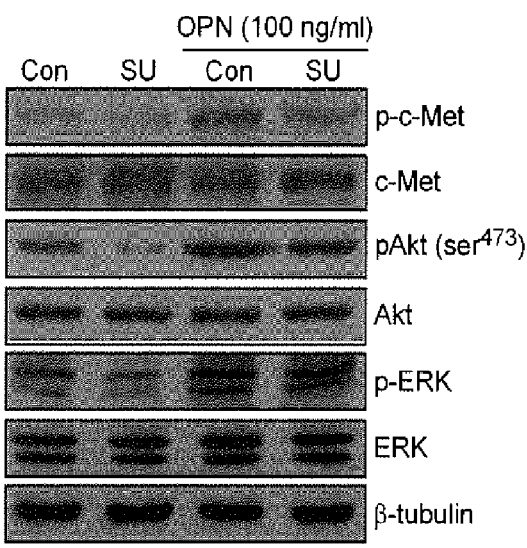

To confirm the link between OPN and c-Met, HepG3 cells were treated with OPN (100 ng/ml) for 24 h in the presence or absence of SU11274. OPN treatment of HepG3 cells significantly activated c-Met, Akt and ERK (FIG. 12F). Co-treatment with SU11274 resulted in significant inhibition of both basal and OPN-induced activation of c-Met and Akt (FIG. 12F). In the control group p-Akt/Akt ratio was 0.58 which was markedly downregulated to 0.05 upon SU11274 treatment. Treatment with OPN increased p-Akt/Akt ratio to 1.42 which was decreased to 0.63 upon SU11274 treatment. SU11274 treatment resulted in partial inhibition of basal and OPN-induced activation of ERK indicating that OPN might activate ERK independent of c-Met activation.

Figure 13A:
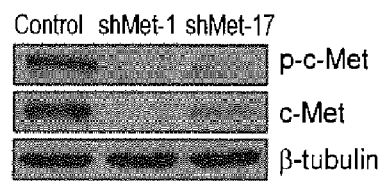
FIGS. 13A-F. Genetic inhibition of c-Met by shRNA blocks LSF function. LSF-17-Consh-15 (Control) is a clone of LSF-17 cells stably expressing control scrambled shRNA and LSF-17-shMet-1 (shMet-1) and LSF-17-shMet-17 (shMet-17) are clones of LSF-17 cells stably expressing c-Met shRNA. A. Expression of the indicated proteins was detected in the indicated cells by Western blot analysis. Cell viability (B) and Matrigel invasion (C) assays were performed with the indicated cells. D. QGY-7703 cells were transfected with control scrambled siRNA (siCon) or c-Met siRNA (siMet) and cell viability was measured by MTT assay. The inset shows Western blot analysis to detect effective knockdown of c-Met by the siRNA. E. Matrigel invasion assay of QGY-7703 cells transfected with control or c-Met siRNA. For B-E, data represent mean±SEM. F. The expression of the indicated proteins was detected in the indicated cells by Western blot analysis. Asterisk (*) represents statistically significant difference (p<0.05).
Figure 13B:
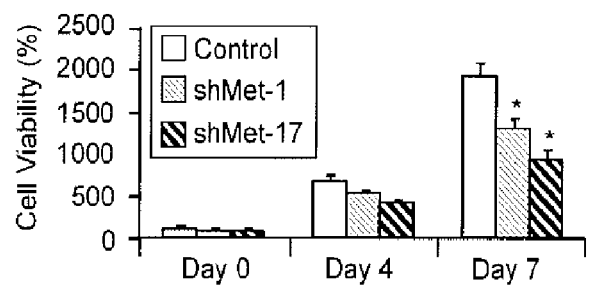
Figure 13C:
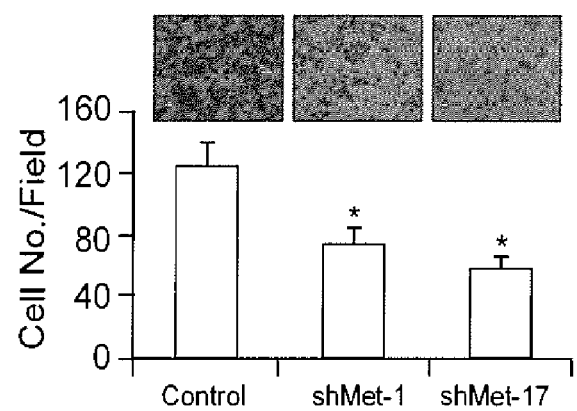
Figure 13D:
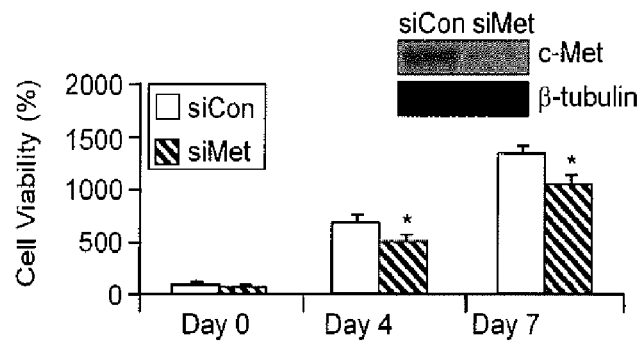
Figure 13E:
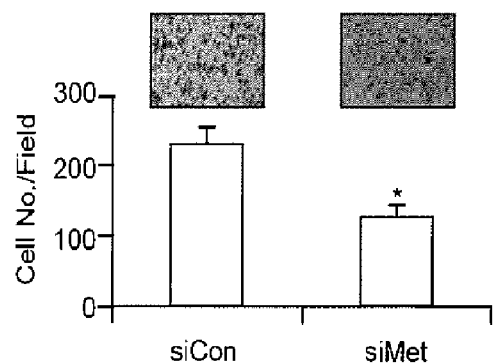

The findings with the chemical inhibitors were further confirmed by genetic means by establishing clones of LSF-17 cells stably expressing c-Met shRNA (LSF-17-shMet-1 and LSF-17-shMet-17). Compared to the Control clone (LSF17-Consh-15) both total and activated c-Met levels were profoundly downregulated in LSF-17-shMet-1 and LSF-17-shMet-17 clones (FIG. 13A). Cell viability and Matrigel invasion was significantly inhibited in LSF-17-shMet-1 and LSF-17-shMet-17 clones compared to the Control clone (FIGS. 13B and 13C, respectively). Similarly, transient transfection of c-Met siRNA to QGY-7703 cells also resulted in profound c-Met downregulation (FIG. 13D, inset), and inhibition of cell viability (FIG. 13D) and Matrigel invasion (FIG. 13E). These findings indicate that c-Met plays an important role in mediating in vitro phenotypes conferred by LSF.

Figure 13F:
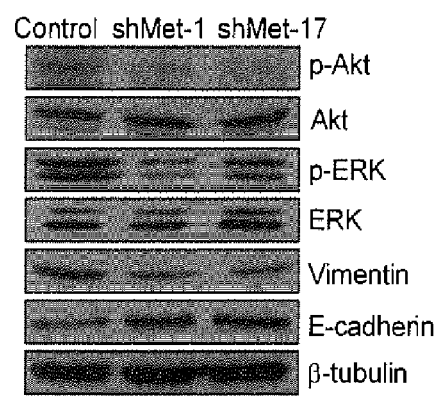
Figure 14A:
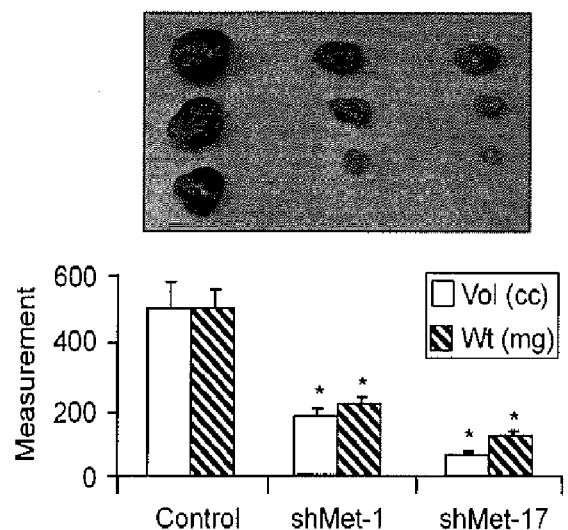
FIGS. 14A-E Inhibition of c-Met blocks LSF-mediated tumorigenesis and metastasis in vivo. A. The indicated cells were subcutaneously implanted in athymic nude mice. Tumor volume and tumor weight were measured 3 weeks after implantation. The inset shows representative tumors at the end of the study. B. The expression of the indicated proteins was detected in tumor sections from Control and shMet-17 cells by immunohistochemical analysis. Arrows in the panel of CD31 staining denote microvessels. Arrows in the panel of H & E staining indicate areas of necrosis. C. Apoptotic (TUNEL positive) cells were detected in tumor sections induced by the indicated cell type. D. The indicated cells were intravenously injected into athymic nude mice and tumors were allowed to develop for 3 weeks. Inset: Top panel, macroscoptic tumors in the animals (arrow). Bottom panel, sections of the lungs showing microscopic tumor nodule (arrow). Graphical representation of the number of metastatic nodules. For, A, C and D, data represent mean±SEM. E. A schematic representation of c-Met activation by LSF and OPN. See text for details. Asterisk (*) represents statistically significant difference (p<0.05).
Figure 14B:
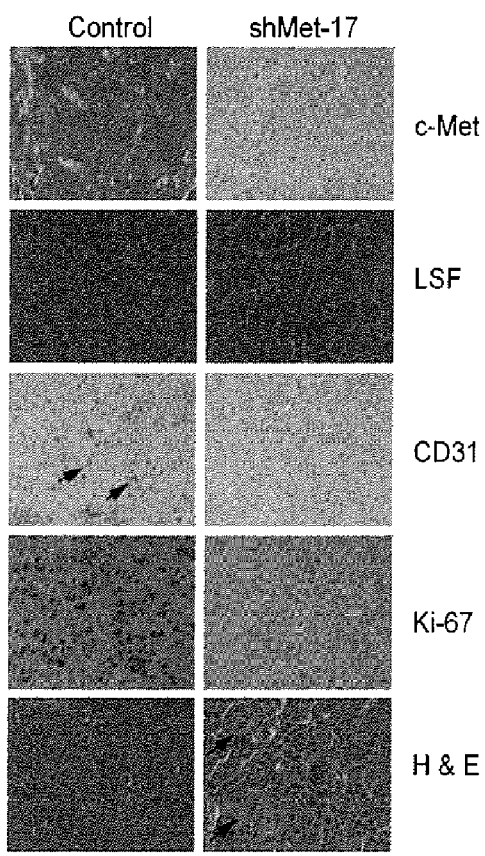
Figure 14C:
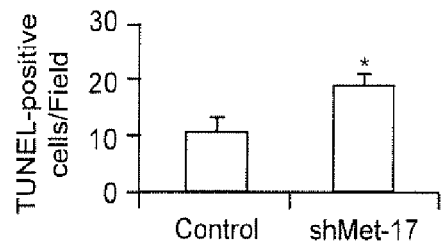
Figure 14D:
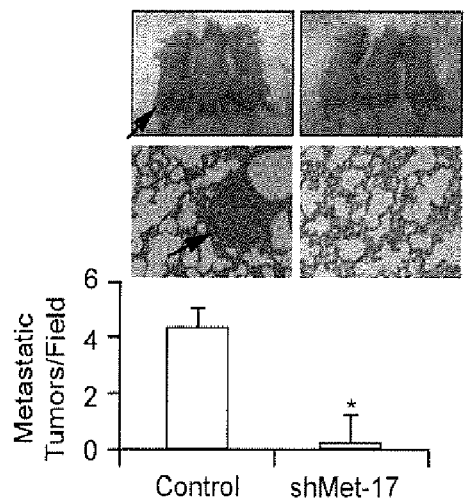

Activation of Akt was significantly inhibited and activation of ERK was moderately suppressed in LSF-17-shMet-1 and LSF-17-shMet-17 clones compared to the Control clone (FIG. 13F). c-Met is a known inducer of EMT and therefore we analyzed the expression of EMT-associated genes upon c-Met knockdown. There was signification downregulation of Vimentin and upregulation of E-cadherin in the LSF-17-shMet-1 and LSF-17-shMet-17 clones compared to the Control clone indicating a reversal of EMT phenotype (FIG. 13F). The in vitro findings demonstrating the importance of c-Met activation in mediating LSF function were further confirmed by in vivo assays. Compared to the Control clone, LSF-17-shMet-1 and LSF-17-shMet-17 clones formed distinctly smaller tumors when the cells were subcutaneously implanted in athymic nude mice (FIG. 14A). Tumors arising from LSF-17-shMet-17 clone showed areas of necrosis upon Hematoxylin & Eosin (H & E) staining (arrows, lowest panels, FIG. 14B). Immunohistochemical analysis of the tumors revealed marked downregulation of c-Met, the angiogenesis marker CD31 and the proliferation marker Ki-67 in sections of tumors arising from LSF-17-shMet-17 clone compared to the Control clone (FIG. 14B). LSF expression was unchanged in both clones indicating that c-Met inhibition could abrogate the oncogenic functions of LSF (FIG. 14B). A significant increase in apoptotic TUNEL-positive cells was detected in the tumors arising from the LSF-17-shMet-17 clone compared to the Control clone (FIG. 14C). However, the increase in apoptosis was not as profound as the inhibition of tumor growth indicating that inhibition of proliferation and angiogenesis might play a major role in growth inhibition of LSF-17-shMet-17 tumors. The metastatic ability of these clones was analyzed by the tail vein metastasis assay. When injected intravenously the Control clone formed multi-organ metastatic tumors, which were visible macroscopically from outside the animals (FIG. 14D, top panel, arrow). However, no metastatic tumors were formed by intravenous injection of the LSF17-shMet-17 cells. Analysis of lung sections indicated microscopic nodules throughout the lungs (FIG. 14D, bottom panel, arrow) in the Control clone injected animals, but very few lung nodules were detected in animals receiving the LSF17-shMet-17 clone.

Discussion

Figure 14E:
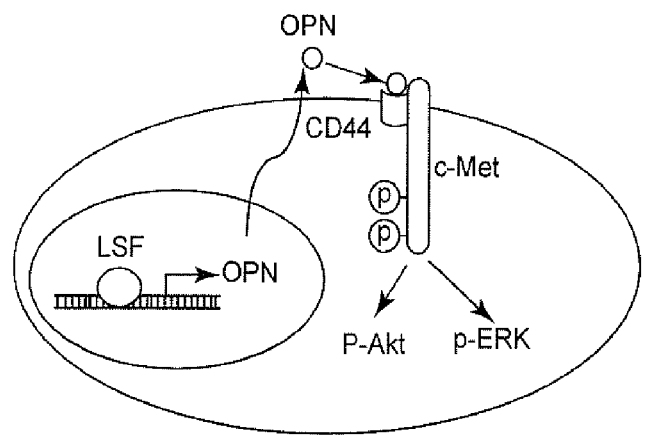

Although LSF was first cloned in 1987 as a cellular transcription factor no prior studies implicated LSF in carcinogenesis [15, 16]. Our finding that LSF functions as an oncogene for HCC and mediates its action by transcriptionally upregulating OPN was the first report connecting LSF to the carcinogenesis process [3] (see Example 1 above). In this Example 2, we significantly extend those observations by documenting that LSF-induced secreted OPN profoundly activates c-Met, an important mediator of EMT, invasion and metastasis [6]. Our activated RTK array analysis identified robust activation of c-Met in LSF-overexpressing cells. LSF did not increase total c-Met level nor did it increase the level of its ligand HGF, thus ruling out two of the most common mechanisms of c-met activation. We focused on OPN as a potential activator of c-Met, since there was one report in the literature [17] demonstrating c-Met activation upon OPN treatment of human mammary epithelial cells. Interestingly, OPN has been shown to be transcriptionally induced by HGF in murine liver cells and to mediate HGF-induced invasive growth [18, 19]. We found that treatment of HepG3 cells with OPN resulted in sustained and robust activation of c-Met. Since both c-Met and OPN can signal through CD44 receptors [4, 6] we reasoned that CD44 might be the common factor controlling OPN-induced c-Met activation. The extracellular domain of CD44 is required for c-Met autophosphorylation while the intracellular domain of CD44 recruits the ezrin, radixin and moesin (ERM) proteins to the HGF-c-Met-CD44 complex [11, 12]. The recruitment of ERM proteins leads to activation of guanine nucleotide exchange factor Sos that activates Ras and MEK/ERK. Binding of OPN to CD44 activates PLCγ, PKC and the PI3K-Akt pathway [4]. We propose a pathway in which OPN might replace HGF initiating interaction between CD44 and c-Met leading to Met autophosphorylation and activation. Indeed, our studies with neutralization antibodies documented that inhibition of CD44, and not the other OPN receptor αvβ3 integrin, prevented OPN-induced c-Met activation. We demonstrated that in the absence of OPN, CD44 and c-Met interact. However, in the presence of OPN the association of phospho-c-Met with CD44 increased. This observation was documented in HepG3 cells that express very low levels of OPN under serum-free conditions to remove potential contributions of OPN in the serum-containing medium as well as in LSF-17 and QGY-7703 cells. These findings indicate that binding of OPN to CD44 might lead to a conformational change in c-Met thereby resulting in autophosphorylation of c-Met in Y1234 and Y1235 residues in the catalytic domain (FIG. 14E). We observed that inhibition of c-Met in LSF17 cells resulted in greater suppression of Akt activation, compared to suppression of ERK activation, indicating that OPN-CD44-c-Met signaling predominantly activates PI3K/Akt signaling. What adapter proteins get recruited to c-Met to activate this important signaling cascade upon OPN binding to CD44 is an area we are currently exploring.

Inhibition of c-Met profoundly abrogated LSF functions, including in vitro proliferation and Matrigel invasion, and in vivo tumor growth, angiogenesis and metastasis, confirming the importance of c-Met activation in mediating LSF action. In clinical HCC samples, we observed a statistical correlation between LSF, OPN, and activated c-Met levels, further strengthening the significance of our findings. LSF is overexpressed in greater than 90% of human HCC samples compared to normal liver. As such, inhibition of either LSF or its downstream mediators, such as OPN or c-Met, will provide an effective strategy to counteract the pathogenesis of HCC, as well as other cancers. Indeed, a Phase I clinical trial using a specific c-Met inhibitor GSK089 for liver cancer [13] is now ongoing and our present findings strongly support the rationale for this potential therapeutic approach. However, a small molecule inhibitor that might bind to the DNA-binding domain of LSF and inhibit its transcriptional activity could also be a good way to block LSF, OPN and c-Met and might represent a potent HCC therapeutic. Such inhibitors can be identified as discussed above.

REFERENCES FOR EXAMPLE 2

1. Parkin D M, Bray F, Ferlay J, Pisani P. Global cancer statistics, 2002. CA: Cancer J Clin 2005; 55: 74-108.
2. Pang R W, Joh J W, Johnson P J, Monden M, Pawlik T M, Poon R T. Biology of hepatocellular carcinoma. Ann Surgical Oncol 2008; 15: 962-971.
3. Yoo B K, Emdad L, Gredler R, Fuller C, Dumur C I, Jones K H, et al. Transcription factor Late SV40 Factor (LSF) functions as an oncogene in hepatocellular carcinoma. Proc Natl Acad Sci USA; 107: 8357-8362.
4. Bellahcene A, Castronovo V, Ogbureke K U, Fisher L W, Fedarko N S. Small integrin-binding ligand N-linked glycoproteins (SIBLINGs): multifunctional proteins in cancer. Nature Rev 2008; 8: 212-226.
5. Yoo B K, Gredler R, Vozhilla N, Su Z-Z, Chen D, Forcier T, et al. Identification of genes conferring resistance to 5-fluorouracil. Proc Natl Acad Sci USA 2009; 106: 12938-12943.
6. Boccaccio C, Comoglio P M. Invasive growth: a MET-driven genetic programme for cancer and stem cells. Nature Rev 2006; 6: 637-645.
7. Birchmeier C, Birchmeier W, Gherardi E, Vande Woude G F. Met, metastasis, motility and more. Nat Rev Mol Cell Biol 2003; 4: 915-925.
8. Trusolino L, Comoglio P M. Scatter-factor and semaphorin receptors: cell signalling for invasive growth. Nature Rev 2002; 2: 289-300.
9. Boccaccio C, Sabatino G, Medico E, Girolami F, Follenzi A, Reato G, et al. The MET oncogene drives a genetic programme linking cancer to haemostasis. Nature 2005; 434: 396-400.
10. Wang R, Ferrell L D, Faouzi S, Maher J J, Bishop J M. Activation of the Met receptor by cell attachment induces and sustains hepatocellular carcinomas in transgenic mice. J Cell Biol 2001; 153: 1023-1034.
11. Orian-Rousseau V, Chen L, Sleeman J P, Herrlich P, Ponta H. CD44 is required for two consecutive steps in HGF/c-Met signaling. Genes Dev 2002; 16: 3074-3086.
12. Orian-Rousseau V, Morrison H, Matzke A, Kastilan T, Pace G, Herrlich P, et al. Hepatocyte growth factor-induced Ras activation requires ERM proteins linked to both CD44v6 and β-actin. Mol Biol Cell 2007; 18: 76-83.
13. Naran S, Zhang X, Hughes S J. Inhibition of HGF/MET as therapy for malignancy. Expert Opin Ther Targets 2009; 13: 569-581.
14. Yoo B K, Emdad L, Su Z Z, Villanueva A, Chiang D Y, Mukhopadhyay N D, et al. Astrocyte elevated gene-1 regulates hepatocellular carcinoma development and progression. J Clin Invest 2009; 119: 465-477.
15. Powell C M, Rudge T L, Zhu Q, Johnson L F, Hansen U. Inhibition of the mammalian transcription factor LSF induces S-phase-dependent apoptosis by downregulating thymidylate synthase expression. Embo J 2000; 19: 4665-4675.
16. Veljkovic J, Hansen U. Lineage-specific and ubiquitous biological roles of the mammalian transcription factor LSF. Gene 2004; 343: 23-40.
17. Tuck A B, Elliott B E, Hota C, Tremblay E, Chambers A F. Osteopontin-induced, integrin-dependent migration of human mammary epithelial cells involves activation of the hepatocyte growth factor receptor (Met). J Cell Biochem 2000; 78: 465-475.
18. Ariztia E V, Subbarao V, Solt D B, Rademaker A W, Iyer A P, Oltvai Z N. Osteopontin contributes to hepatocyte growth factor-induced tumor growth and metastasis formation. Experimental cell research 2003; 288: 257-267.
19. Medico E, Gentile A, Lo Celso C, Williams T A, Gambarotta G, Trusolino L, et al. Osteopontin is an autocrine mediator of hepatocyte growth factor-induced invasive growth. Cancer Res 2001; 61: 5861-5868.

Example 3

Small Molecule Inhibition of LSF Inhibits Tumor Growth In Vivo

Figure 15A:
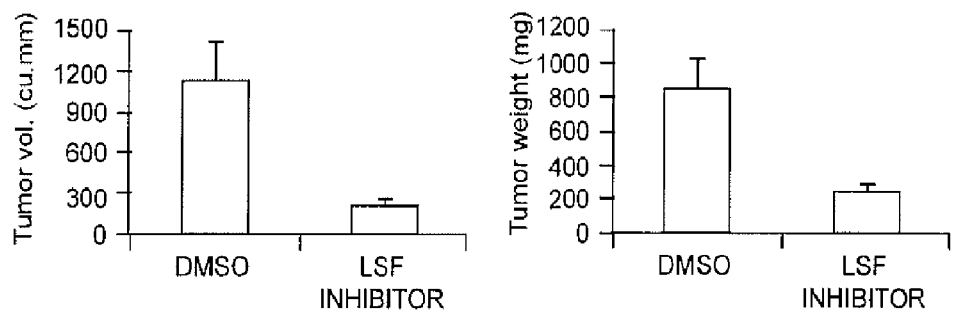
FIGS. 15A-B. Effects of administration of LSF inhibitor on tumors in vivo. Tumor volume (left panel) and tumor weight (right panel) were measured at the end of the study. The data represents mean±SEM. B. Immunofluorescence analysis of the indicated proteins in the tumor sections.

The observations presented in Examples 1 and 2 led us to test the effects of administration of an LSF inhibitor on tumor growth and development in vivo.
Materials and Methods
Tumor Xenograft Studies:
Subcutaneous xenografts were established into the flanks of athymic nude mice using QGY-7703 cells ($5 \times 10^5$). Ten (10) animals per group were used in this study. When the tumors reached a volume of ~100 mm$^3$ (requiring about a week) i.p. injection of a small molecule chemical LSF inhibitor (2 µM) was given 5 times once every 3 days over a period of 2 weeks. The animals were followed for another 2 weeks at which point they were sacrificed. Tumor volume was measured twice weekly with a caliper and calculated using the formula π6× larger diameter×(smaller diameter).
Immunofluorescence:
Formalin-fixed paraffin-embedded tumor sections were deparaffinized and were permeabilized with 0.1% TritonX-100 in PBS for 30 minutes. Sections were then blocked for 1 h at room temperature with 2% goat serum and 1% BSA in PBS and incubated with anti-LSF (1:200; mouse monoclonal; BD Biosciences), anti-OPN (1:200; mouse monoclonal; Santa Cruz Biotechnology), anti-Ki-67 (1:200; mouse monoclonal; BD Biosciences) and anti-CD31 (1:200, mouse monoclonal, Dako) antibodies overnight at 4° C. Sections were then rinsed in PBS and incubated with the corresponding secondary antibody for 1 hr at room temperature. The sections were analyzed by an immunofluorescence microscope (Olympus).
Results The results are presented in FIGS. 15A and B. As can be seen in FIG. 15A, there was a profound inhibition of tumor growth in LSF inhibitor-treated animals compared to DMSO-treated control animals. The treated animals did not show any signs of toxicity indicating its safety of use, thus establishing safety and efficacy for the treatment of HCC tumors in vivo.

Figure 15B:
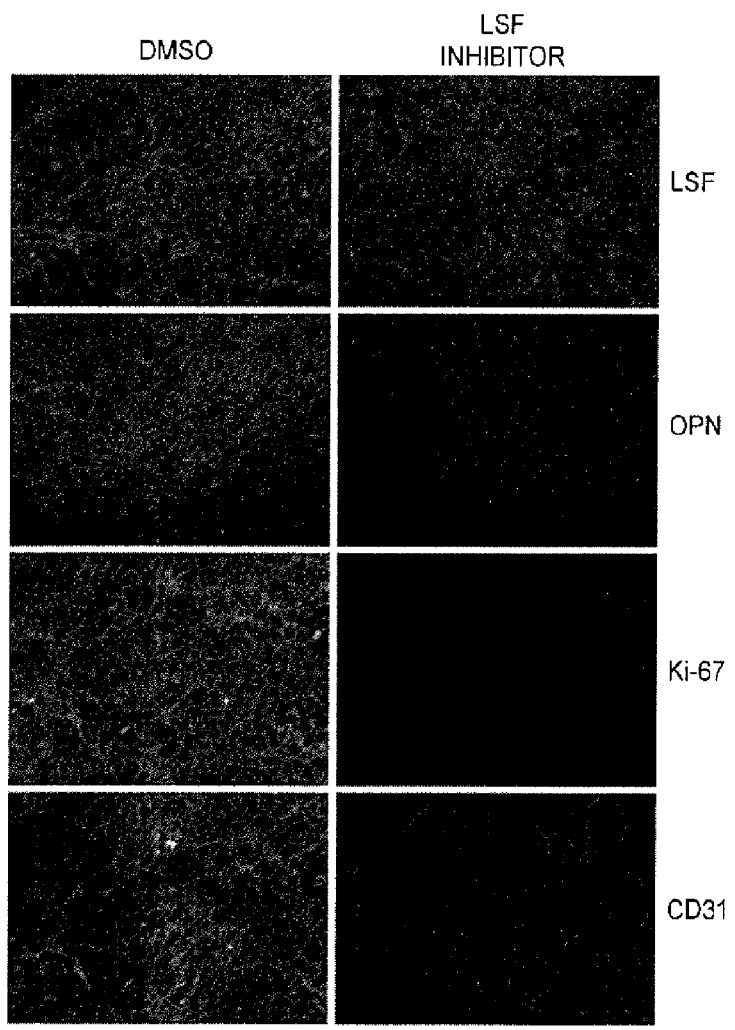

Formalin-fixed paraffin-embedded tumor sections were analyzed for expression of a number of proteins by immunofluorescence assay (FIG. 15B). The LSF inhibitor did not affect LSF expression itself indicating that it is an inhibitor of LSF function not expression. This is supported by the finding that there was marked downregulation of osteopontin (OPN), a key mediator of LSF function which is transcriptionally regulated by LSF, in treated animals compared to the DMSO-treated control group. There was marked decrease in the expression of the proliferation marker Ki-67 and angiogenesis marker CD31, measuring microvessel density, in the group treated with LSF inhibitor, compared to the control DMSO-treated group.

These findings demonstrate that the administration of small molecule chemical LSF inhibitors is an effective approach for treating HCC in vivo.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of inhibiting or reducing tumor growth associated with cancer in vivo in a subject, comprising the step of limiting expression or activity of Late SV40 Factor (LSF) activity in vivo in said subject, wherein said LSF inhibitor compound targets at least one DNA binding domain of LSF.

2. The method of claim 1, wherein said cancer is hepatocellular carcinoma (HCC).

3. The method of claim 1, wherein said at least one DNA binding domain of LSF is an osteopontin (OPN) promoter binding domain.

4. A method of promoting damage or death of cancer cells in vivo in a subject, comprising the step of limiting expression or activity of Late SV40 Factor (LSF) activity in vivo in said subject, and wherein said step of limiting includes a step of administering to said subject one or more of an LSF inhibitor compound, anti-LSF inhibitory RNA, and anti-LSF antibodies, and wherein said LSF inhibitor compound targets at least one DNA binding domain of LSF.

5. The method of claim 4, wherein said cancer cells are from hepatocellular carcinoma.

6. The method of claim 4, wherein said at least one DNA binding domain of LSF is an osteopontin (OPN) promoter binding domain.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 1
acacgcttat gcgggtatgt                                           20

<210> SEQ ID NO 2
<211> LENGTH: 20
<212> TYPE: DNA
<213> ORGANISM: Artificial Sequence

```
<220> FEATURE:
<223> OTHER INFORMATION: synthetic oligonucleotide primer

<400> SEQUENCE: 2
gaacatttgg taggggggaaa                                              20
```